US012776396B2

(12) United States Patent
Thompson, IV et al.

(10) Patent No.: US 12,776,396 B2
(45) Date of Patent: Oct. 27, 2026

(54) PHENOTYPING OF CLINICAL NOTES USING NATURAL LANGUAGE PROCESSING MODELS

(71) Applicant: Tempus AI, Inc., Chicago, IL (US)

(72) Inventors: William E. Thompson, IV, Denver, CO (US); David Michael Vidmar, Amherst, MA (US); RuiJun Chen, Livingston, NJ (US)

(73) Assignee: Tempus AI, Inc., Chicago, IL (US)

( * ) Notice: Subject to any disclaimer, the term of this patent is extended or adjusted under 35 U.S.C. 154(b) by 526 days.

(21) Appl. No.: 18/497,835

(22) Filed: Oct. 30, 2023

(65) Prior Publication Data

US 2024/0145050 A1 May 2, 2024

Related U.S. Application Data

(60) Provisional application No. 63/420,466, filed on Oct. 28, 2022.

(51) Int. Cl.
*G16H 10/60* (2018.01)
*G06F 16/353* (2025.01)
(Continued)

(52) U.S. Cl.
CPC ........... *G16H 10/60* (2018.01); *G06F 16/353* (2019.01); *G06F 40/284* (2020.01); *G16H 50/70* (2018.01)

(58) Field of Classification Search
CPC ...... G16H 10/60; G16H 50/70; G06F 16/353; G06F 40/284
(Continued)

(56) References Cited

U.S. PATENT DOCUMENTS 8,898,798 B2 * 11/2014 Rogers .................. G06Q 10/10 726/28
12,278,004 B2 * 4/2025 Novak .................. G16H 40/20
(Continued)

OTHER PUBLICATIONS

Regular expression syntax cheat sheet, mdn web docs, Retrieved from the Internet: <URL: https://developer.mozilla.org/en-US/docs/Web/JavaScript/Guide/Regular_Expressions/Cheatsheet, [retrieved on Apr. 19, 2024], pp. 1-7.
(Continued)

*Primary Examiner* — Cam Linh T Nguyen
(74) *Attorney, Agent, or Firm* — MORGAN, LEWIS & BOCKIUS LLP

(57) ABSTRACT

Systems and methods for phenotyping clinical data are provided. The method includes obtaining episodic records comprising unstructured clinical data from an electronic medical record (EMR) or electronic health record (EHR) for patients. The method also includes filtering the episodic records by language pattern recognition to identify episodic records that each includes an expression related to a clinical condition. The method also includes splitting each episodic record to obtain snippets comprising tokens. The method also includes predicting if an episodic record represents an instance of the clinical condition using a trained classifier. The trained classifier includes an aggregation function that aggregates the snippets to output a corresponding representation for the episodic record, and an interpretation function that interprets the corresponding representation to output a corresponding prediction for whether the episodic record represents an instance of the clinical condition.

21 Claims, 20 Drawing Sheets

(51) Int. Cl.
*G06F 40/284* (2020.01)
*G16H 50/70* (2018.01)

(58) Field of Classification Search
USPC .......................................................... 707/737
See application file for complete search history.

(56) References Cited

U.S. PATENT DOCUMENTS

| | | | | |
|---|---|---|---|---|
| 2016/0371457 | A1* | 12/2016 | Zillner | G16Z 99/00 |
| 2019/0034590 | A1 | 1/2019 | Oren et al. | |
| 2022/0068432 | A1* | 3/2022 | Ruderfer | G16B 20/10 |
| 2023/0395209 | A1* | 12/2023 | Riskin | G16H 10/20 |

OTHER PUBLICATIONS

Bekker, Jessa et al. “Learning From Positive and Unlabeled Data: A Survey”, Machine Learning (2020) 109, https://arxiv.org/pdf/1811.04820.pdf, pp. 719-760.
Devlin, Jacob et al. “BERT: Pre-training of Deep Bidirectional Transformers for Language Understanding”, Google AI Language, Cornell University, Oct. 11, 2018, pp. 1-16.
Gunel, Beliz et al. “Supervised Contrastive Learning for Pre-Trained Language Model Fine-Tuning”, Published as a conference paper at ICLR 2021, https://openreview.net/pdf?id=cu7IUiOhujH, pp. 1-15.
Haris, M. Syauqi et al. “Automated Features Extraction from Software Requirements Specification (SRS) Documents as The Basis of Software Product Line (SPL) Engineering”, Journal of Information Technology and Computer Science, vol. 5, No. 3, Dec. 2020, pp. 279-292.
Huang, Kexin et al. “An Interpretable End-to-end Fine-tuning Approach for Long Clinical Text”, Machine Learning for Health (ML4H) 2020, ML4H Extended Abstract Arxiv Index, pp. 1-5.
Kaplan, Jared et al. “Scaling Laws for Neural Language Models”, Johns Hopkins University, OpenAI, 2020, https://arxiv.org/pdf/2001.08361.pdf, pp. 1-30.
Rokach, Lior et al. “Negation recognition in medical narrative reports”, Inf Retrieval (2008) 11, pp. 499-538.
Wan, Shaohua, et al. “Bootstrapping Face Detection with Hard Negative Examples”, Aug. 9, 2016, Xioaomi Inc., pp. 1-7.
Xue, Linting et al. “ByT5: Towards a token-free future with pre-trained byte-to-byte models”, arxiv 2022, https://arxiv.org/abs/2105.13626, pp. 1-16.

* cited by examiner

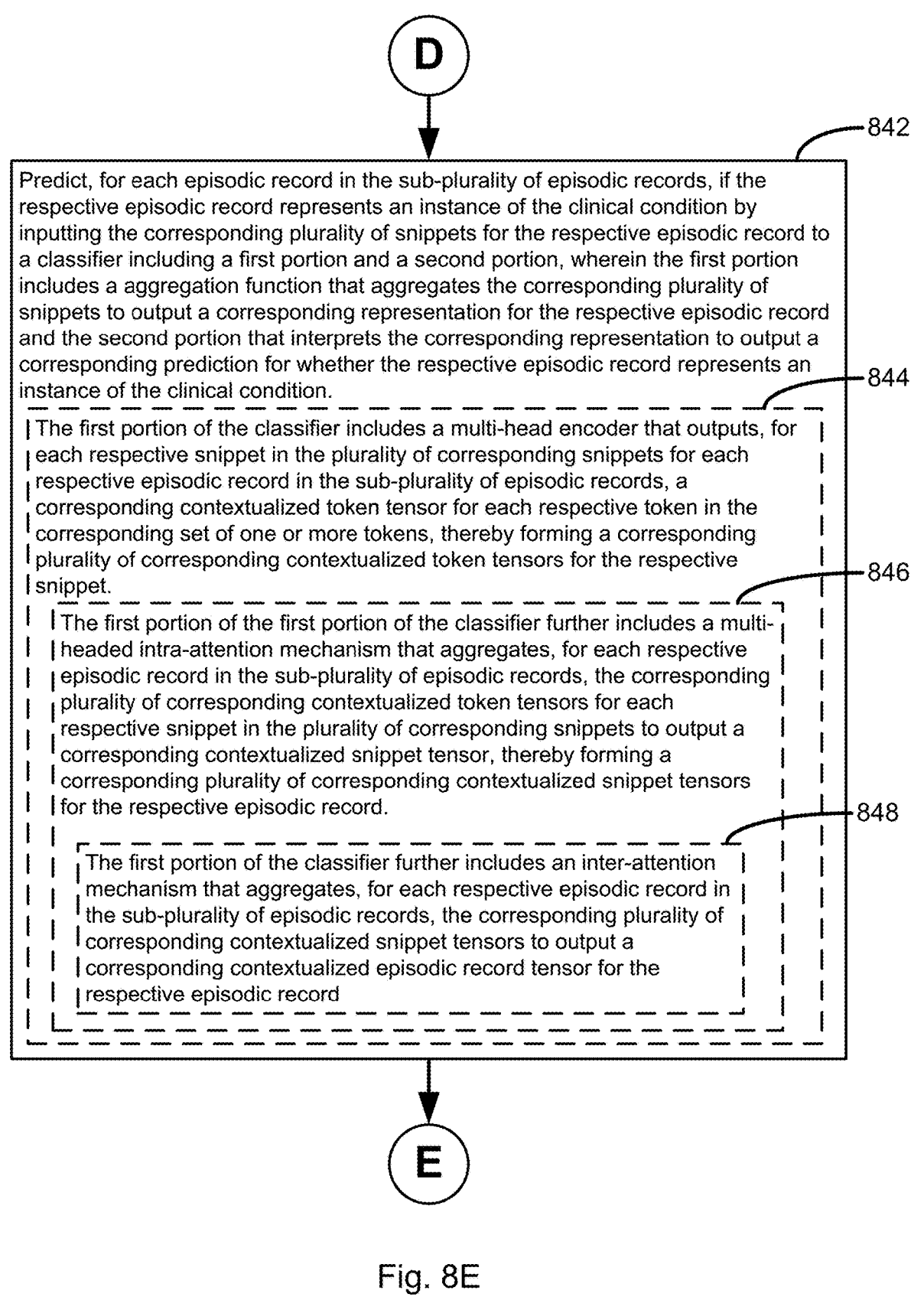

D

842

Predict, for each episodic record in the sub-plurality of episodic records, if the respective episodic record represents an instance of the clinical condition by inputting the corresponding plurality of snippets for the respective episodic record to a classifier including a first portion and a second portion, wherein the first portion includes a aggregation function that aggregates the corresponding plurality of snippets to output a corresponding representation for the respective episodic record and the second portion that interprets the corresponding representation to output a corresponding prediction for whether the respective episodic record represents an instance of the clinical condition.

844

The first portion of the classifier includes a multi-head encoder that outputs, for each respective snippet in the plurality of corresponding snippets for each respective episodic record in the sub-plurality of episodic records, a corresponding contextualized token tensor for each respective token in the corresponding set of one or more tokens, thereby forming a corresponding plurality of corresponding contextualized token tensors for the respective snippet.

846

The first portion of the first portion of the classifier further includes a multi-headed intra-attention mechanism that aggregates, for each respective episodic record in the sub-plurality of episodic records, the corresponding plurality of corresponding contextualized token tensors for each respective snippet in the plurality of corresponding snippets to output a corresponding contextualized snippet tensor, thereby forming a corresponding plurality of corresponding contextualized snippet tensors for the respective episodic record.

848

The first portion of the classifier further includes an inter-attention mechanism that aggregates, for each respective episodic record in the sub-plurality of episodic records, the corresponding plurality of corresponding contextualized snippet tensors to output a corresponding contextualized episodic record tensor for the respective episodic record

E

Fig. 8E

PHENOTYPING OF CLINICAL NOTES USING NATURAL LANGUAGE PROCESSING MODELS

CROSS-REFERENCE TO RELATED APPLICATIONS

This application claims the benefit of U.S. Provisional Application No. 63/420,466, filed on Oct. 28, 2022, which is expressly incorporated by reference in its entirety for all purposes.

TECHNICAL FIELD

This application is directed to using natural language processing models to phenotype clinical notes.

BACKGROUND

An interaction between a patient and a healthcare provider is logged in a patient record, for example an electronic health record (EHR) or a hand-written record which may be later digitized to generate an electronic medical record (EMR). EHRs and EMRs are then stored in electronic medical system curated for the healthcare provider. These EHRs and EMRs typically have structured data, including medical codes used by the healthcare provider for billing purposes, and unrestructured data, including clinical notes and observations made by physicians, physician assistants, nurses, and others while attending to the patient.

In bulk, EHRs and EMRs hold a tremendous amount of clinical data that, in theory, can be leveraged to the great benefit of publica health. For example, the CDC estimates that in 2019 nearly 90% of office-based physicians used an EHR or EMR system to track patient treatment. 2019 National Electronic Health Records Survey public use file national weighted estimates, CDC/National Center for Health Statistics. Such wealth of clinical data could be used to generate models for predicting disease risk, predicting treatment outcomes, recommending personalized therapies, predicting disease-free survival following treatment, predicting disease recurrence, and the like.

However, in order for this data to be available for model training, each electronic record needs to be properly labeled with one or more clinical phenotypes on which the record holds data. Conventionally, this is done using one or both of (i) a computer-implemented rules-based model that evaluates medical codes in the structured data portion of the electronic record, and (ii) manual chart inspection. However, these methods perform rather poorly. Specifically, conventional rules-based models perform poorly at least because EHR and EMR systems are not standardized across the healthcare industry, meaning that data is presented differently across the numerous records systems in the industry. Moreover, these models cannot account for the inconsistent use of medical codes across different medical practices and healthcare providers, such that the rules do not generalize across different EHR and EMR systems and/or different healthcare providers with different coding practices. Manual review, on the other hand, is very tedious and time consuming. Manual review of a single health record typically takes 30-60 minutes, which becomes prohibitively slow and expensive when performed across tens of millions, hundreds of millions, or billions of electronic medical records. Moreover, manual review is also subject to the bias of the reviewer.

SUMMARY

Given the above background, what is needed in the art are improved methods and systems for phenotyping electronic health records at appropriate scale. The present disclosure addresses these and other problems by using natural language processing to evaluate clinical notes contained in unstructured portions of electronic health records for relevant phenotypes. The disclosed systems and methods both improve performance of electronic medical record phenotyping and facilitate scaling such phenotyping across large amounts of clinical data for improved generalizability.

Accordingly, one aspect of the present disclosure provides a phenotyping of clinical notes. In some embodiments, the method includes obtaining, in electronic form, a plurality of episodic records, wherein each respective episodic record in the plurality of episodic records includes corresponding unstructured clinical data from an electronic medical record (EMR) or electronic health record (EHR) for a respective patient in a plurality of patients.

In some embodiments, the method includes obtaining, for a respective episodic record in the plurality of episodic records, the corresponding unstructured clinical data from a plurality of medical evaluations memorialized in the EMR or EHR for the respective patient.

In some embodiments, the method includes selecting the plurality of medical evaluations by clustering all or a portion of medical evaluations memorialized in the EMR or EHR for the respective patient to obtain one or more corresponding medical evaluation clusters and aggregating unstructured clinical data corresponding to each respective medical evaluation in a respective medical evaluation cluster of the one or more corresponding medical evaluation clusters, thereby forming the respective episodic record.

In some embodiments, the clustering is, at least in part, temporal based clustering.

In some embodiments, the clustering is one-dimensional clustering.

In some embodiments, the method includes obtaining, for a respective episodic record in the plurality of episodic records, the corresponding unstructured clinical data from a single of medical evaluation memorialized in the EMR or EHR.

In some embodiments, each episodic record in the plurality of episodic records does not include corresponding structured clinical from the EMR or EHR.

In some embodiments, the method includes filtering the plurality of episodic records by language pattern recognition to identify a sub-plurality of episodic records that each includes an expression related to a clinical condition in the corresponding unstructured clinical data.

In some embodiments, the language pattern recognition includes, for each respective episodic record in the plurality of episodic records, matching one or more regular expressions against the corresponding unstructured clinical data, thereby identifying the sub-plurality of episodic records.

In some embodiments, the language pattern recognition includes a machine learning model trained to identify language related to the clinical condition.

In some embodiments, the clinical condition is atrial fibrillation.

In some embodiments, the method includes splitting, for each respective episodic record in the sub-plurality of episodic records, the corresponding unstructured clinical data into a corresponding plurality of snippets. Each respective snippet in the corresponding plurality of snippets includes a corresponding set of one or more tokens.

In some embodiments, the splitting of the corresponding unstructured clinical data is performed prior to the filtering of the plurality of episodic records.

In some embodiments, the splitting of the corresponding unstructured clinical data is performed after the filtering of the plurality of episodic records.

In some embodiments, each snippet in the corresponding plurality of snippets has approximately a same number of tokens.

In some embodiments, for each respective episodic record in the sub-plurality of episodic records, each respective snippet in the corresponding plurality of snippets has a corresponding number of tokens that is within 25% of the corresponding number of tokens for each other respective snippet in the corresponding plurality of snippets.

In some embodiments, for a respective episodic record in the sub-plurality of episodic records, the splitting the corresponding unstructured clinical data includes tokenizing the corresponding unstructured clinical data to obtain a plurality of tokens, segmenting the plurality of tokens to obtain a plurality of segments, wherein each respective segment in the plurality of segments has approximately a same number of tokens, ranking respective segments in the plurality of segments based on values of tokens within each respective segment, and removing one or more respective segments from the plurality of segments based on the ranking, thereby generating the corresponding plurality of snippets for the respective episodic record.

In some embodiments, for a respective episodic record in the sub-plurality of episodic records, the splitting the corresponding unstructured clinical data includes segmenting the corresponding unstructured clinical data to obtain a plurality of segments, wherein each respective segment in the plurality of segments includes a respective portion of the corresponding unstructured clinical data, tokenizing, in each respective segment in the plurality of segments, the respective portion of the corresponding unstructured clinical data to obtain a plurality of tokenized segments, splitting respective tokenized segments, in the plurality of tokenized segments, having a corresponding number of tokens exceeding a threshold number of tokens to obtain a second plurality of tokenized segments, ranking respective segments in the second plurality of tokenized segments based on values of tokens within each respective tokenized segment, and removing one or more respective tokenized segments from the second plurality of tokenized segments based on the ranking, thereby generating the corresponding plurality of snippets for the respective episodic record.

In some embodiments, for a respective episodic record in the sub-plurality of episodic records, the splitting the corresponding unstructured clinical data includes segmenting the corresponding unstructured clinical data by sentence to obtain a plurality of segments, wherein each respective segment in the plurality of segments includes a respective portion of the corresponding unstructured clinical data, tokenizing, in each respective segment in the plurality of segments, the respective portion of the corresponding unstructured clinical data to obtain a plurality of tokenized segments, splitting respective tokenized segments, in the plurality of tokenized segments, having a corresponding number of tokens exceeding a first threshold number of tokens to obtain a second plurality of tokenized segments, merging respective tokenized segments, in the second plurality of tokenized segments, having a corresponding number of tokens falling below a second threshold number of tokens to obtain a third plurality of tokenized segments, ranking respective segments in the third plurality of tokenized segments based on values of tokens within each respective tokenized segment, and removing one or more respective tokenized segments from the third plurality of tokenized segments based on the ranking, thereby generating the corresponding plurality of snippets for the respective episodic record.

In some embodiments, the ranking is based, at least in part, on a scoring system that rewards the presence of tokens found on a priority list of tokens.

In some embodiments, the scoring system punishes the presence of tokes found on a de-priority list of tokens.

In some embodiments, the corresponding plurality of snippets is a predetermined number of snippets.

In some embodiments, the method includes predicting, for each episodic record in the sub-plurality of episodic records, if the respective episodic record represents an instance of the clinical condition by inputting the corresponding plurality of snippets for the respective episodic record to a classifier including a first portion and a second portion, wherein the first portion includes a aggregation function that aggregates the corresponding plurality of snippets to output a corresponding representation for the respective episodic record and the second portion that interprets the corresponding representation to output a corresponding prediction for whether the respective episodic record represents an instance of the clinical condition.

In some embodiments, the first portion of the classifier includes a multi-head encoder that outputs, for each respective snippet in the plurality of corresponding snippets for each respective episodic record in the sub-plurality of episodic records, a corresponding contextualized token tensor for each respective token in the corresponding set of one or more tokens, thereby forming a corresponding plurality of corresponding contextualized token tensors for the respective snippet.

In some embodiments, the first portion of the classifier further includes a multi-headed intra-attention mechanism that aggregates, for each respective episodic record in the sub-plurality of episodic records, the corresponding plurality of corresponding contextualized token tensors for each respective snippet in the plurality of corresponding snippets to output a corresponding contextualized snippet tensor, thereby forming a corresponding plurality of corresponding contextualized snippet tensors for the respective episodic record.

In some embodiments, the first portion of the classifier further includes an inter-attention mechanism that aggregates, for each respective episodic record in the sub-plurality of episodic records, the corresponding plurality of corresponding contextualized snippet tensors to output a corresponding contextualized episodic record tensor for the respective episodic record In some embodiments, the second portion of the classifier includes a model that outputs, for each respective episodic record in the sub-plurality of episodic records, the corresponding prediction for whether the respective episodic record represents an instance of the clinical condition in response to inputting the corresponding representation for the respective episodic record to the model.

In some embodiments, the second portion of the classifier includes a model selected from the group consisting of a neural network, a support vector machine, a Naive Bayes algorithm, a nearest neighbor algorithm, a boosted trees algorithm, a random forest algorithm, a convolutional neural network, a decision tree, a regression algorithm, and a clustering algorithm.

In some embodiments, the second portion of the classifier includes a linear transform that converts a respective output of the first portion of the classifier, for a respective episodic record in the sub-plurality of episodic records, into a corresponding scalar number that is compared to a threshold to output the corresponding prediction.

In some embodiments, the linear transform is an affine transform.

In some embodiments, the classifier includes at least 500 parameters, at least 1000 parameters, at least 5000 parameters, at least 10,000 parameters, at least 50,000 parameters, at least 100,000 parameters, at least 250,000 parameters, at least 500,000 parameters, at least 1,000,000 parameters, at least 10 M parameters, at least 100 M parameters, at least 1 MM parameters, at least 10 MM parameters, or at least 100 MM parameters.

In some embodiments, the method includes labelling each respective episodic record, in the sub-plurality of episodic records, predicted to represent an instance of the clinical condition to form a set of episodic records, wherein each respective episodic record in the set of episodic records represents an instance of the clinical condition.

In some embodiments, the method includes training a model to predict an outcome of the clinical condition using the set of episodic records.

Another aspect of the present disclosure provides a computer system for phenotyping of clinical notes. The computer system comprises one or more processors and memory addressable by the one or more processors. The memory stores at least one program for execution by the one or more processors. The at least one program comprises instructions for performing any of the methods described herein.

Another aspect of the present disclosure provides a non-transitory computer readable storage medium. The non-transitory computer readable storage medium stores instructions, which when executed by a computer system, cause the computer system to perform any of the methods described herein.

BRIEF DESCRIPTION OF THE DRAWINGS

In the drawings, embodiments of the systems and method of the present disclosure are illustrated by way of example. It is to be expressly understood that the description and drawings are only for the purpose of illustration and as an aid to understanding, and are not intended as a definition of the limits of the systems and methods of the present disclosure.

FIGS. 8A-8G show a flowchart for an example method for phenotyping clinical data in accordance with some embodiments of the present disclosure.

Like reference numerals refer to corresponding parts throughout the several views of the drawings.

DETAILED DESCRIPTION

Figure 1:
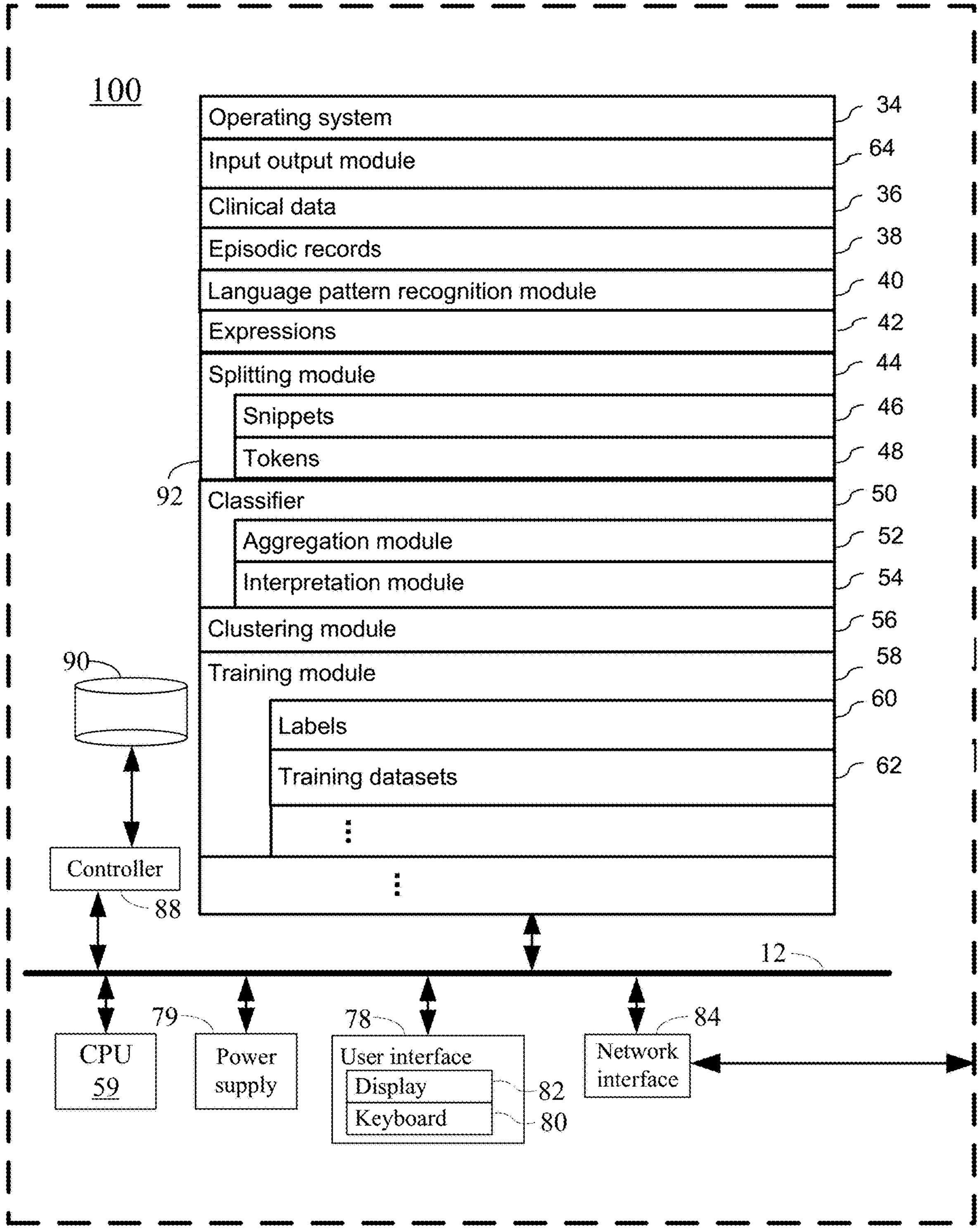
FIG. 1 illustrates a computer system in accordance with some embodiments of the present disclosure.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The present disclosure provides systems and methods for phenotyping clinical notes. In some embodiments, a natural language processing (NLP) model is trained to detect the presence of a clinical condition (e.g., atrial fibrillation) using unstructured clinical notes by learning at scale from labels generated from a validated structured EHR and billing code definition. Such methods facilitate scaling disease label methods across large amounts of clinical data without suffering from differences due to variations in coding practices.

A phenotype corresponds to a list of patient identifiers and diagnosis dates, representing diagnoses of a clinical condition, identified across an EHR. Typically, an expert physician performs a chart review to adjudicate whether a record corresponds to a disease diagnosis. This manual process can be time consuming and error prone. Accordingly, there is a need for automated methods to label the presence of a disease within EHR data. Conventional systems use labels generated from billing code definition (e.g., "at least 2 relevant ICD codes used within 1 year"). Such labels can be accurate within one health system, but fail to generalize across systems due to variations in coding practices.

A phenotype model is any set of rules or transformations which produces a phenotype as output. This includes both hand crafted rules-based approaches and machine learning models. Phenotype models may be used to generate labels for risk prediction models that can predict the risk of certain disease from clinical signals. Phenotype models may also be used for population health monitoring, and for identifying prior history of a disease.

Conventional phenotype models do not generalize to new systems with different coding practices. Such models may be limited to relatively simple rule combinations which can cause low performance, and/or may be susceptible to bias (e.g., model bias due to expert's biases about relevant diagnosis codes). Existing phenotypes for cardiovascular diseases are largely dependent on code-based definitions, which often suffer from poor sensitivity for low-prevalence diseases and poor generalizability. High-quality EHR phenotypes and disease labels are essential for evidence generated from cohort studies and predictions from machine learning models.

Conventional phenotype models ignore clinical notes despite the fact that key signals (e.g., symptoms) are often present only in such notes. Clinical notes are typically long. Curators take on an average half an hour to read through and analyze event level information in clinical notes. These notes are also sparse, meaning much of this information is irrelevant. The meaning of any given clinical term is context-dependent. A clinical term could be confirmatory, negated, past history, family history, suspected, or risk factor. Much of the text is in clinical shorthand, so important phrases can be represented in many different ways. There can be conflicting information, as the clinical narrative unfolds and diagnoses change (particularly with differential diagnoses).

It will be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

FIG. 1 illustrates a computer system 100 for phenotyping of clinical notes, according some embodiments. In typical embodiments, computer system 100 comprises one or more computers. For purposes of illustration in FIG. 1, the computer system 100 is represented as a single computer that includes all of the functionality of the disclosed computer system 100. However, the present disclosure is not so limited. The functionality of the computer system 100 may be spread across any number of networked computers and/or reside on each of several networked computers and/or virtual machines. One of skill in the art will appreciate that a wide array of different computer topologies are possible for the computer system 100 and all such topologies are within the scope of the present disclosure.

Turning to FIG. 1 with the foregoing in mind, the computer system 100 comprises one or more processing units (CPUs) 59, a network or other communications interface 84, a user interface 78 (e.g., including an optional display 82 and optional keyboard 80 or other form of input device), a memory 92 (e.g., random access memory, persistent memory, or combination thereof), one or more magnetic disk storage and/or persistent devices 90 optionally accessed by one or more controllers 88, one or more communication busses 12 for interconnecting the aforementioned components, and a power supply 79 for powering the aforementioned components. To the extent that components of memory 92 are not persistent, data in memory 92 can be seamlessly shared with non-volatile memory 90 or portions of memory 92 that are non-volatile or persistent using known computing techniques such as caching. Memory 92 and/or memory 90 can include mass storage that is remotely located with respect to the central processing unit(s) 59. In other words, some data stored in memory 92 and/or memory 90 may in fact be hosted on computers that are external to computer system 100 but that can be electronically accessed by the computer system 100 over an Internet, intranet, or other form of network or electronic cable using network interface 84. In some embodiments, the computer system 100 makes use of models that are run from the memory associated with one or more graphical processing units in order to improve the speed and performance of the system. In some alternative embodiments, the computer system 100 makes use of models that are run from memory 92 rather than memory associated with a graphical processing unit.

The memory 92 of the computer system 100 stores:

- an operating system 34 that includes procedures for handling various basic system services;
- an input output module 64 for obtaining in electronic form, episodic records that include corresponding unstructured clinical data from one or more electronic medical records (EMR) or electronic health records (EHR) for patients. In some embodiments, the input output module 64 labels episodic records predicted to represent an instance of the clinical condition to form a set of episodic records. In some embodiments, the input output module 64 trains a model to predict an outcome of the clinical condition using the episodic records that are labelled;
- clinical data 36 that includes unstructured data, and optionally structured data (e.g., billing codes). The unstructured data may include unstructured clinical data from an electronic medical record (EMR) or electronic health record (EHR) for patients;
- episodic records 38 that include unstructured clinical data from an electronic medical record (EMR) or electronic health record (EHR) for a respective patient in a plurality of patients;
- a language pattern recognition module 40 for filtering the episodic records 38 using language pattern recognition to identify episodic records that include an expression related to a clinical condition. In some embodiments, the language pattern recognition module 40 matches one or more regular expressions against corresponding unstructured clinical data. In some embodiments, the language pattern recognition includes a machine learning model trained to identify language related to the clinical condition;
- expressions 42 that may include regular expressions for use by the language pattern recognition module 40. The expressions 42 may be optional in systems that use a machine learning model for language pattern recognition;

- a splitting module 44 that includes snippets 46 and tokens 48. The splitting module 44 splits unstructured clinical data for an episodic record into corresponding snippets. Each snippet includes a corresponding set of tokens, which may include lexical tokens, such as words. The individual token and snippet representations may include vectors and are sometimes referred to as embeddings. The cumulation or concatenation of these vectors or embeddings constitutes a tensor. The snippets and tokens may be referred to as tensors, because the snippets and/or tokens are typically batched and concatenated during training;
- a classifier 50 that includes an aggregation module 52 (sometimes referred to as a first portion of the classifier 50) and an interpretation module 54 (sometimes referred to as the second portion of the classifier 50). The first portion includes an aggregation function that aggregates corresponding snippets for an episodic record to output a corresponding representation. The second portion interprets the corresponding representation to output a corresponding prediction for whether the episodic record represents an instance of a clinical condition. The aggregation module 52 and the interpretation module 54 include respective parameters (e.g., parameters obtained from training machine learning models);
- optionally, a clustering module 56 for clustering medical evaluations memorialized in an EMR or EHR for a patient to obtain medical evaluation clusters. The clustering module 56 also aggregates unstructured clinical data corresponding to each medical evaluation in a respective medical evaluation cluster, thereby forming a respective episodic record. In some embodiments, the clustering uses temporal based clustering (e.g., based on the dates of the medical evaluations memorialized in the EMR or HER). In some embodiments, the clustering is one-dimensional clustering; and
- optionally, a training module 58 that includes labels 60 and a training dataset 52, for training the classifier 50.

In some implementations, one or more of the above identified data elements or modules of the computer system 100 are stored in one or more of the previously mentioned memory devices, and correspond to a set of instructions for performing a function described above. The above identified data, modules or programs (e.g., sets of instructions) need not be implemented as separate software programs, procedures or modules, and thus various subsets of these modules may be combined or otherwise re-arranged in various implementations. In some implementations, the memory 92 and/or 90 optionally stores a subset of the modules and data structures identified above. Furthermore, in some embodiments the memory 92 and/or 90 stores additional modules and data structures not described above. Details of the modules and data structures identified above are further described below in reference to FIGS. 2-8.

Figure 2:
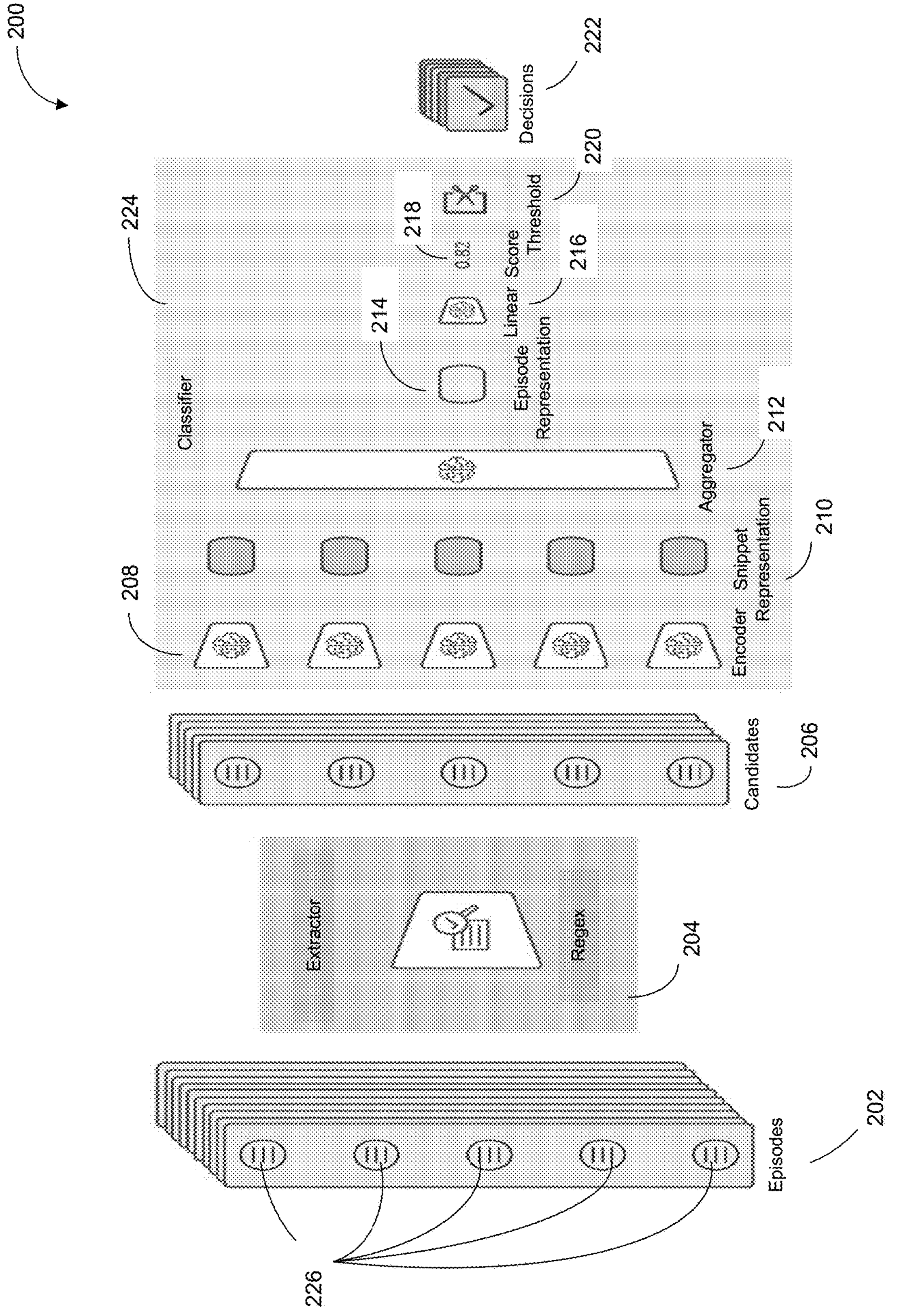
FIG. 2 shows a schematic diagram of a system for phenotyping clinical data in accordance with some embodiments of the present disclosure.

FIG. 2 shows a schematic diagram of a system 200 for phenotyping clinical data, according to some embodiments. The system 200 may be implemented using a computer system (e.g., the computer system 100 shown and described above in reference to FIG. 1). The system 200 is sometimes referred to as the extractor-classifier network.

Some embodiments preprocess clinical notes. Some embodiments use long clinical notes (e.g., approximately 100,000 words) to use state-of-the-art pre-trained models with a word limit (e.g., 512 words) without having to throw away context. In some embodiments, the clinical notes are aggregated to episodes 202. An encounter includes an interaction between a patient and a healthcare provider that results in the logging of clinical notes into an EHR system. An episode 202 includes a cluster of encounters representing a single hospital stay. Typically, a single hospital stay is logged into multiple encounters. Some embodiments determine, for each patient, episode boundaries using one-dimensional clustering (e.g., kernel density estimation (KDE)) on encounter date. In some embodiments, notes between boundaries are aggregated together.

Episodes 202 are input to an extractor 204 (e.g., the language pattern recognition module 40) to obtain candidate episodes 206 (sometimes referred to as candidates). In some embodiments, the extractor 204 uses regular expressions for filtering data. For example, the extractor may use the following regular expression for AFib: (?i) atrial fibrillation|\Wafib\W|\saf\s|\Wa.fib\W|atrial flutter|aflutter|\Wa.flutter\W. In some embodiments, the extractor 204 uses regular expression to filter a set of clinical notes for model decisioning to only those that likely mention a clinical condition.

With conventional machine learning models, it may take more than 0.1 seconds per episode for inference, without some form of filtering. The extractor 204 reduces training and inference time significantly, fixes compute budget, and eliminates training-serving skew. Specifically, the sheer number of notes to be run through a machine learning model is reduced by at least an order of magnitude, saving compute cost. Additionally, the extractor increases the generalizability of the classifier by reducing the effect of training-serving skew (difference between model performance during training and performance during serving or inference). This helps focus the classifier 224 on a narrower task of discerning positive mentions versus incidental mentions (e.g., "this patient has afib" versus "the patient has a family history of afib"). In some experiments, the extractor 204 showed 92% sensitivity and 22% positive predictive value (PPV). The 92% sensitivity is a conservative estimate, chart review estimates pushed the sensitivity close to 98%. High recall ensures that majority of the positive cases are captured. Low precision is not a problem. The classifier 224 is trained to explicitly weed out the false positives out of the candidate pool. Training data prevalence is extractor PPV.

Figure 3:
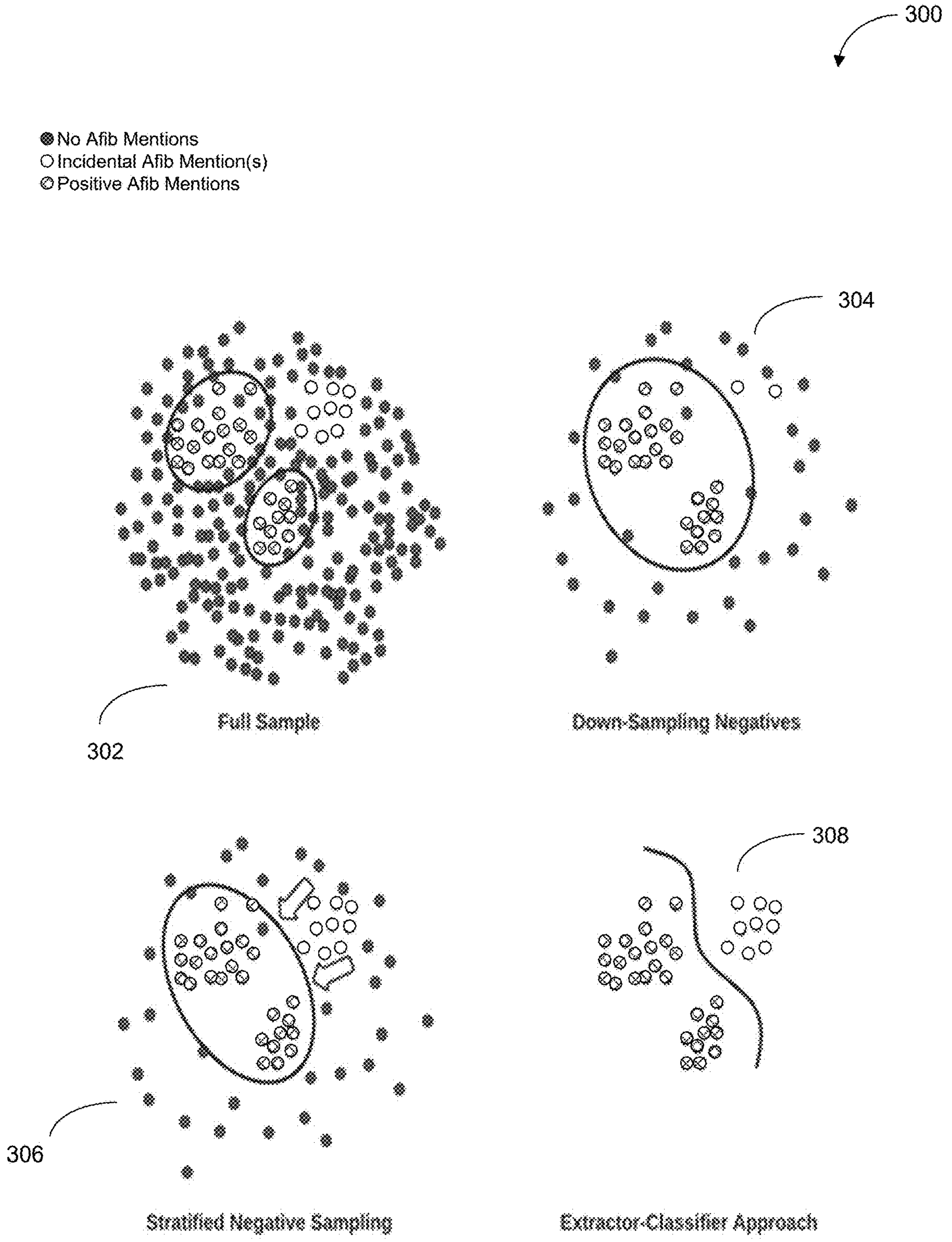
FIG. 3 shows an example comparison between different techniques for phenotyping clinical notes in accordance with some embodiments of the present disclosure.

FIG. 3 shows an example comparison 300 between different techniques for phenotyping clinical notes, according to some embodiments. Suppose the goal is to predict whether an episode includes an instance of the clinical condition AFib. A full sample 302 includes three classes—no AFib mentions (shown in red color), incidental AFib mentions (shown in blue color) and positive AFib mentions (shown in green color). Down-sampling negatives 304 results in including some no AFib mentions, and stratified negative sampling 306 is not sufficient to narrow the boundary between the three classes. On the other hand, the extractor-classifier network 200 that uses the extractor 204 produces results 308 that differentiates between incidental AFib mentions and positive AFib mentions.

Referring back to FIG. 2, episode text may be too large to feed into deep learning models. Accordingly, some embodiments segment or split the text (e.g., the unstructured text corresponding to each episode) into roughly even snippets 226, taking sentence boundaries into account. Some embodiments rank and trim text according to a number of medically-relevant words in each snippet. Some embodiments limit number of snippets and/or words per snippets (e.g., a maximum size of 512 snippets of 256 words, totaling 131,072 words).

Figure 4A:
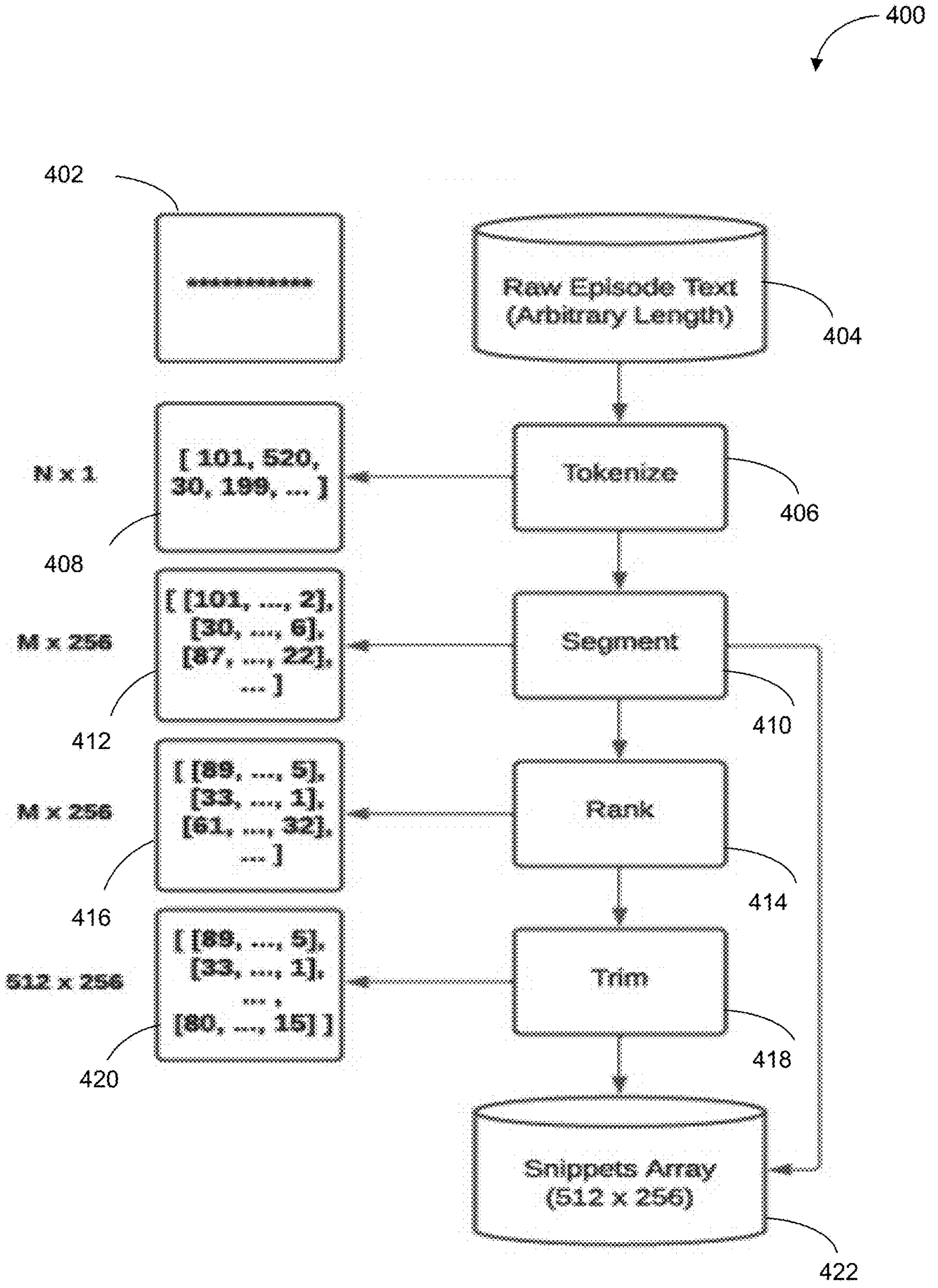
FIGS. 4A, 4B and 4C show example methods for segmenting or splitting text, in accordance with some embodiments of the present disclosure.
Figure 4B:
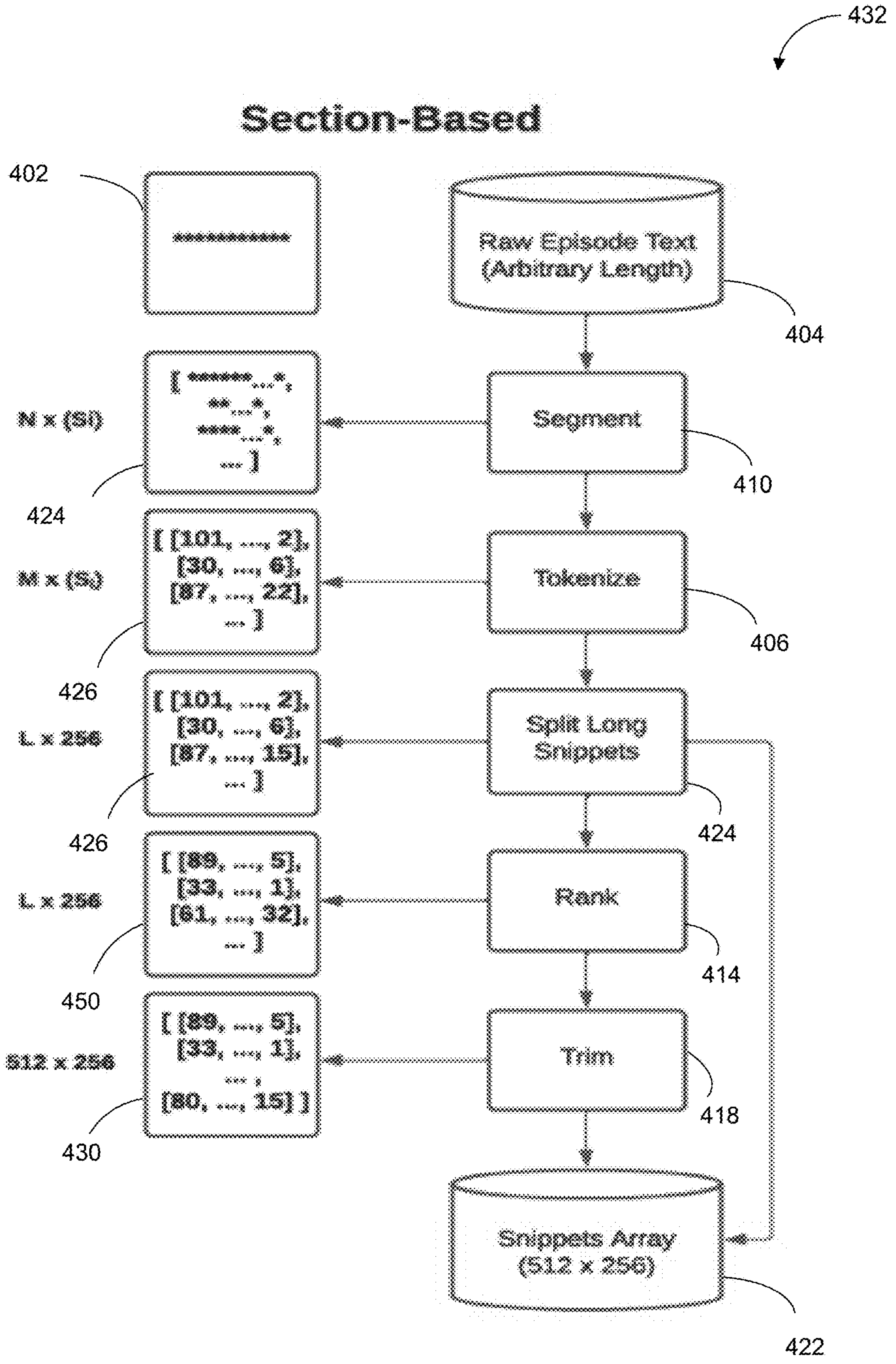
Figure 4C:
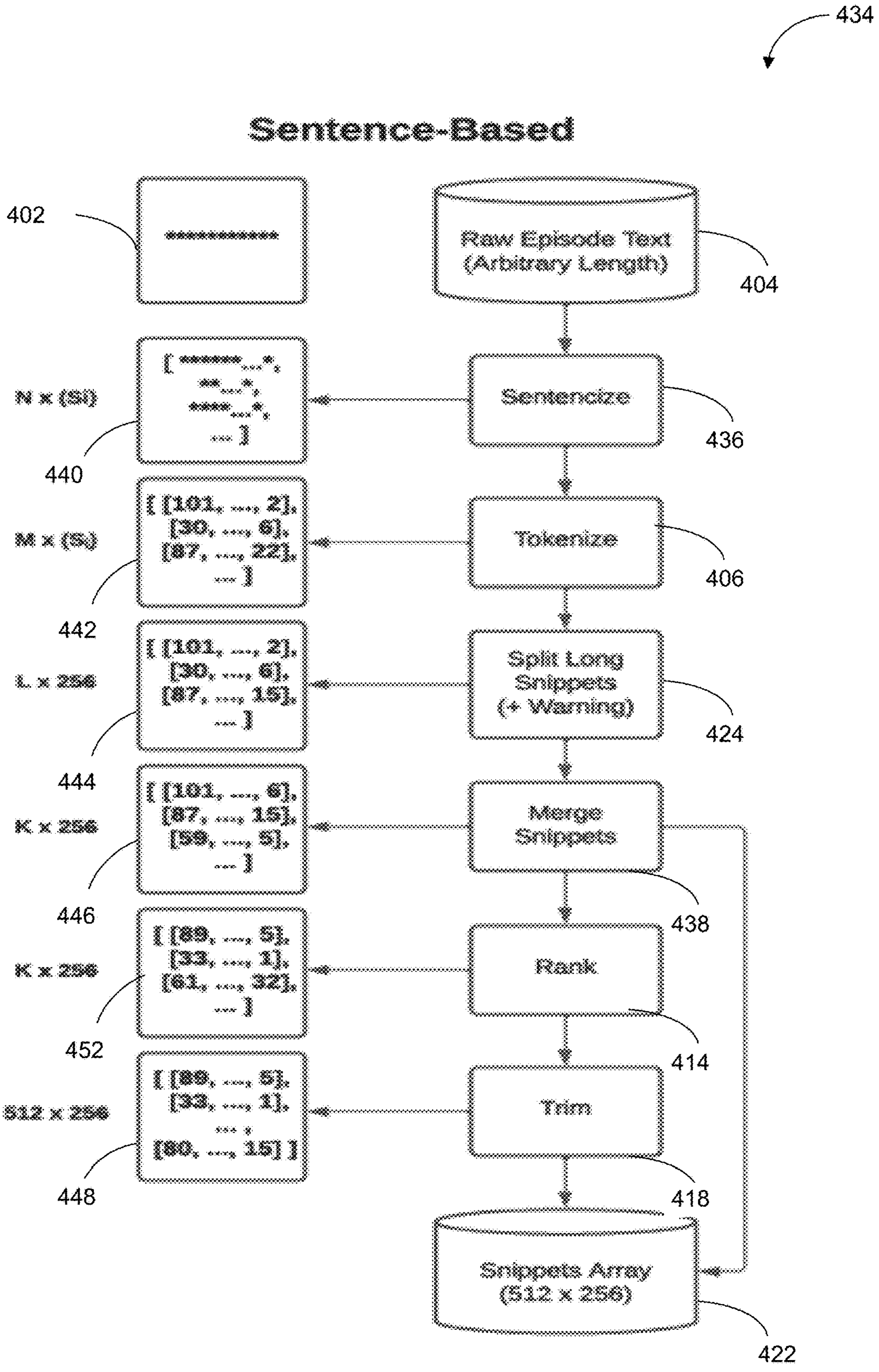

FIGS. 4A, 4B and 4C show example methods for segmenting or splitting text, according to some embodiments. FIG. 4A shows an example basic method 400 for splitting text. A database 404 stores raw episode text 402, which has an arbitrary length. This raw text is tokenized (406) to produce a list 408 of N tokens. This list is segmented (410) or split into M segments 412, each segment having a predetermined number of tokens (256 in this example). The segments are ranked (414) to obtain an ordered list 416 of the segments. The ordered list is subsequently trimmed (418) to obtain a predetermined number of segments 420 (in this example, there are 512 segments with 256 tokens in each segment) that may be stored in a snippets array 422. This method is not site-specific. For example, the raw text may be obtained from any number of sites which contributed to an EHR data (or aggregated from a number of EHR systems). Because the splitting step is agnostic to sections, a section that includes a text "no AFib" may be split into two snippets, one having a token corresponding to "no" and another including a token corresponding to "AFib". The method may rank (414) based on number of tokens in a priority list and/or tokens in a de-priority list.

FIG. 4B shows another example method 432 for splitting, according to some embodiments. This method performs the segment step 410 before the tokenize step 406. The raw text 402 is segmented (410) to obtain text segments 414, totaling N segments, each having a predetermined segment length $S_i$. These segments are tokenized (406) to obtain M times S i segments. These tokenized segments are split (424) to avoid long snippets. In this example, some segments (e.g., the segment [87, . . . , 22]) is split into multiple segments. The resulting segments (L segments, each with 256 tokens, in this example) are ranked (414) to obtain an ordered list of segments 450, which is subsequently trimmed (418) to obtain a reduced number of snippets 430 that may be stored in the snippets array 422. This methos is less likely to split sections, and is more likely to keep coherent thoughts together. However, this method requires curating reasonably generalizable rules for the splitting and may result in more thrown away snippets, since some snippets may include far less than 256 tokens. Some embodiments split the raw text into roughly even snippets of given size (e.g., 256 tokens). Some embodiments avoid cutting a snippet in the middle of a sentence, by first cutting text into sentences and then combining neighboring sentences to get roughly a same number of token snippets (e.g., 256 token snippets).

FIG. 4C shows yet another example method 434 which performs sentence-based splitting, according to some embodiments. Raw text 402 is sentencized (436) to obtain N number of sentences 440, which is tokenized (406) to obtain M sets of tokens 442. Long snippets (any set in the M sets) are split to obtain L sets, each set having a predetermined number of tokens (256 in this example). Some embodiments may generate a warning to alert a user regarding long snippets. Some short snippets may be merged (438) to obtain a candidate set of snippets 446, which is ranked (414) to obtain an ordered list and trimmed (418) to obtain a trimmed set of snippets 448 that is stored in the snippets array 422. This example method is similar to the one shown in FIG. 4A in that the method is also not site-specific. The method does not require any specific rule for splitting or merging other than the ones described above, and helps generate close to a predetermined number of token snippets. However, the method aggregates different sections so it requires appropriate sentencization.

In some embodiments, regular expression filtering is used to split raw text 402. An example of regular expression syntax that can be used to split raw text into sentences is "e\s{2,}1(?<!\w\-\\0(?<![A-Z][a-z]\.)(?<=\0.1\?)\s'." In some embodiments, particular punctuation marks are excluded from being identified as sentence boundaries. For example, the period at the end of the abbreviation 'Dr.' for doctor can be excluded (e.g., "dr. XX"). Examples of regular expression syntax useful for excluding identification of particular punctuation as sentence boundaries is found, for example, in Section 3.2.2. of Rokach L. et al., Information Retrieval Journal, 11(6):499-538 (2008), the content of which is incorporated herein by reference, in its entirety, for all purposes.

In some embodiments, a machine learning model is used to split raw text into sentences. As described in Haris, M S et al., Journal of Information Technology and Computer Science, 5(3):279-92, incorporated herein by reference in its entirety for all purposes, known NLP libraries, including Google SyntaxNet, Stanford CoreNLP, NLTK Phyton library, and spaCy implement various methods for sentencization.

Conventional systems pass snippets into a pre-trained model (e.g., Bidirectional Encoder Representations from Transformers (BERT)) and then aggregate via a snippet-level attention (described below). These systems only keep snippets that contain any regular expression hits. There are a number of drawbacks to the conventional approach. First, since the conventional systems use an arbitrary window around the regular expression hit to define the snippet, those techniques are losing potentially important context for the model to learn. Second, given that those conventional systems only focus on snippets that mention any of the regular expressions, other important findings in the notes are lost. In contrast, the extractor described herein identifies entire episodes that may have a single regular expression hit. So very little information is dropped or left out and the additional information or context allows the model to learn to identify which snippets are most important. This improved methodology likely improves model generalizability.

Referring back to FIG. 2, an encoder 208 (e.g., a pre-trained model, such as BERT) encodes the candidates 206 to a snippet representation 210, which is input to an aggregator 212 to obtain an episode representation 214. The episode representation 214 is subsequently input to a linear component 216 that computes a score (e.g., a value between 0 and 1; higher the score, higher the match). A threshold 220 is applied to this score 218 to obtain decisions 222. Each decision corresponds to an episode and indicates whether the episode represents an instance of a clinical condition. The encoder 208, the aggregator 212, the linear component 216, and the threshold 220 are sometimes collectively referred to as a classifier 224, which may be implemented using the classifier module 50. In some embodiments, the linear component or model is an affine transform of the episode representation 214. The transform converts that embedding output into a single number that can be thresholded into a decision between 10,11. Such components are typically used as a last layer in modern neural network classifiers.

In some embodiments, the encoder 208 is a pre-trained BERT model (with pre-trained weights), which outputs a (contextualized) vector for each snippet. In some embodiments, the encoder 208 processes each snippet of a single episode to output a vector representation for each token in each snippet.

In some embodiments, the aggregator 212 aggregates the vectors using attention for a single episode, to obtain the episode representation 214. In some embodiments, an intra-attention mechanism aggregates each token (for a given snippet) into a single vector representation for that snippet. In some embodiments, an inter-attention mechanism aggregates each snippet vector representation from the intra-attention mechanism into a single vector representation for the entire episode. The examples described herein for the attention mechanisms use a vanilla attention, as opposed to self-attention, for the sake of illustration. Any method that aggregates multiple vectors together in a trainable or having learnable parameters may be used. For example, a simple vector sum may be used. In general, learnable aggregation may be implemented using attention or any method that aggregates multiple vectors into a single vector, according to some embodiments.

Attention is a learned weighted sum of a collection of inputs, where this collection can be of arbitrary size. Suppose a machine learning pipeline includes at some point a 3D tensor of shape (N, sequence_length, dim_size), where for each datapoint, there is a sequence_length collection of vectors, each dim_size in length. These vectors may be anything from token embeddings to hidden states along a recurrent neural network (RNN). The ordering of these vectors is not important, although, it is possible to embed that information through positional embeddings. A goal of attention is to encode the original (N, sequence_length, dim_size) shape input into a weighted sum along sequence_length, collapsing it down to (N, dim_size) where each datapoint is represented by a single vector. This output can be useful as an input to another layer or directly as an input to a logistic head.

The attention mechanism is a learned weighted sum of a collection of inputs. Rather than taking a naive sum, an attention layer is trained to pay attention to certain inputs when generating this sum. It keys in on the most important inputs and weighs them more heavily. This is done over multiple attention heads—concurrent attention layers reading over the same input—which are then aggregated into a final summarization. A single attention head can be thought of as a retrieval system with a set of keys, queries and values. The attention mechanism learns to map a query (Q) against a set of keys (K) to retrieve the most relevant input values (V). The attention mechanism accomplishes this by calculating a weighted sum where each input is weighed proportional to its perceived importance (i.e., attention weight). This weighting is performed in all attention heads and then further summarized downstream into a single, weighted representation.

In some embodiments, the attention mechanism is a multi-headed attention mechanism. That is, in some embodiments, each snippet or encoded representation thereof, is input into a different attention head. Having multiple heads allows the attention mechanism to have more degrees of freedom in attempting to aggregate information. Each individual head may focus on a different mode when aggregating; across heads, it should converge to the underlying distribution. Thus, multiple heads helps in allowing the model to focus on different concepts.

Figure 5A:
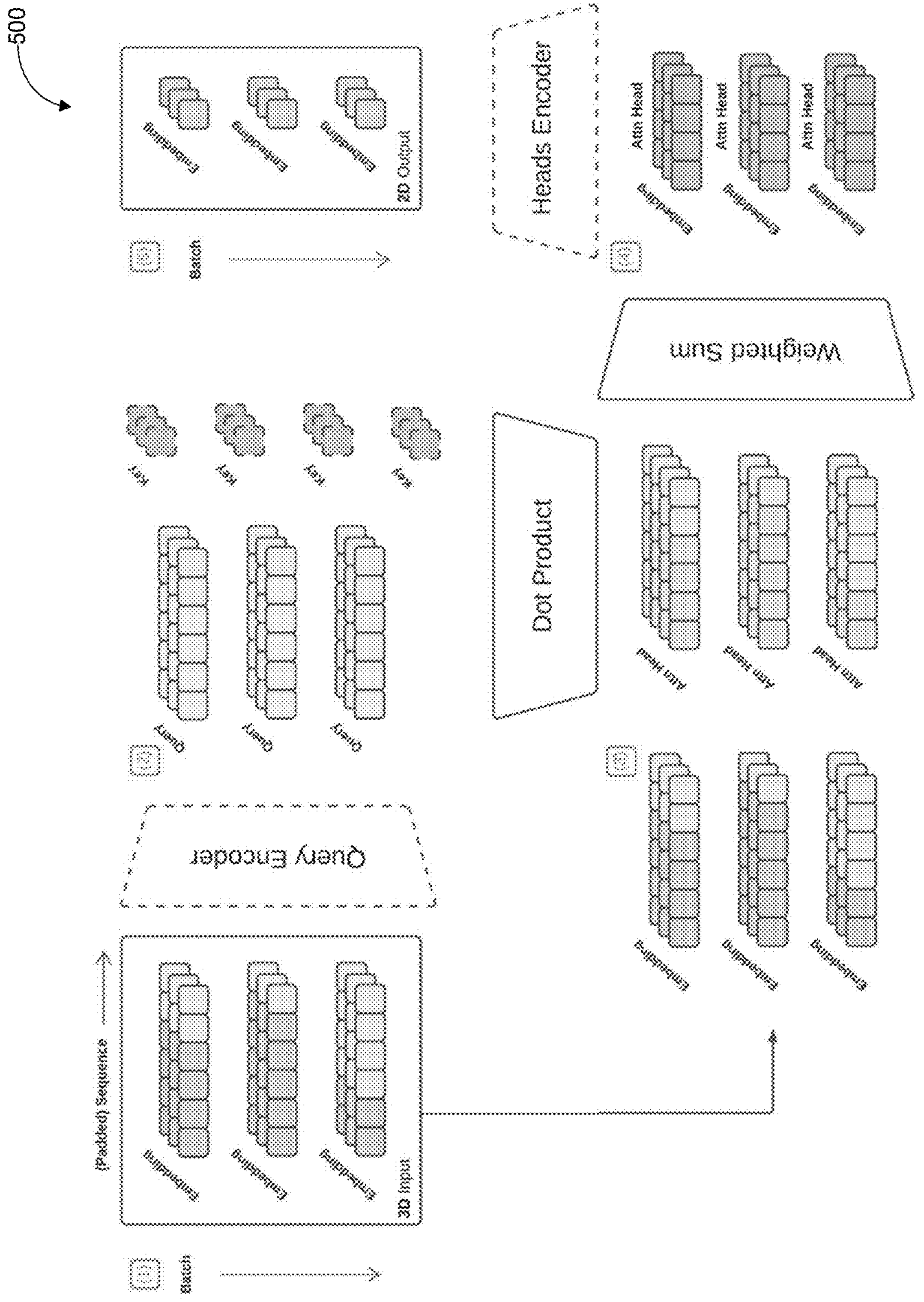
FIG. 5A is a schematic diagram of an example mechanism in accordance with some embodiments of the present disclosure.

FIG. 5A is a schematic diagram of an example mechanism 500, according to some embodiments. In step (1), the mechanism accepts as input a three-dimensional (3D) tensor of shape (batch_size, max_seq_length, dim_model) representing an input as a collection of embeddings where the order does not matter. In most scenarios, a same sized sequence across datapoints is not needed. Often, padding is used to conform to these dimensions (and hence the descriptor maximum sequence length for this dimension). In step (2), for each datapoint, an attention value is calculated by taking the dot product between a set of queries and keys. The final output is a set of attention weights per attention head. Subsequently, a weighted sum is computed. In step (3), each input sequence along max_seq_length is then collapsed into a single representation via a sum of embeddings weighted by the attention weights. This is performed per attention head. In step (4), finally, the attention heads are collapsed via a weighed sum into a single representation. In step (5), the final output is a two-dimensional (2D) tensor of shape (batch_size, dim_model) which represents a single dense representation per datapoint.

Figure 5B:
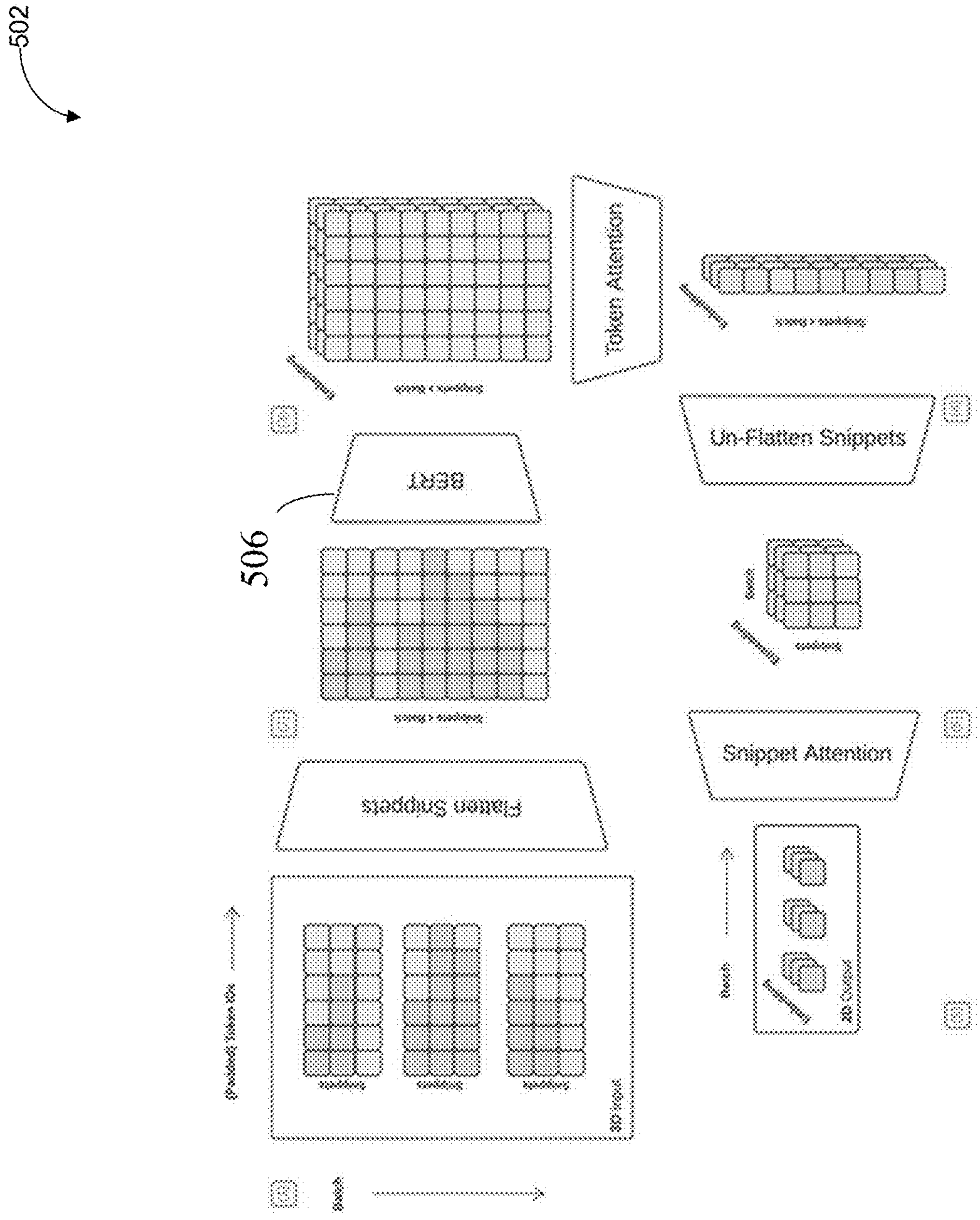
FIG. 5B shows an example architecture with a snippet encoder in accordance with some embodiments of the present disclosure.
Figure 5C:
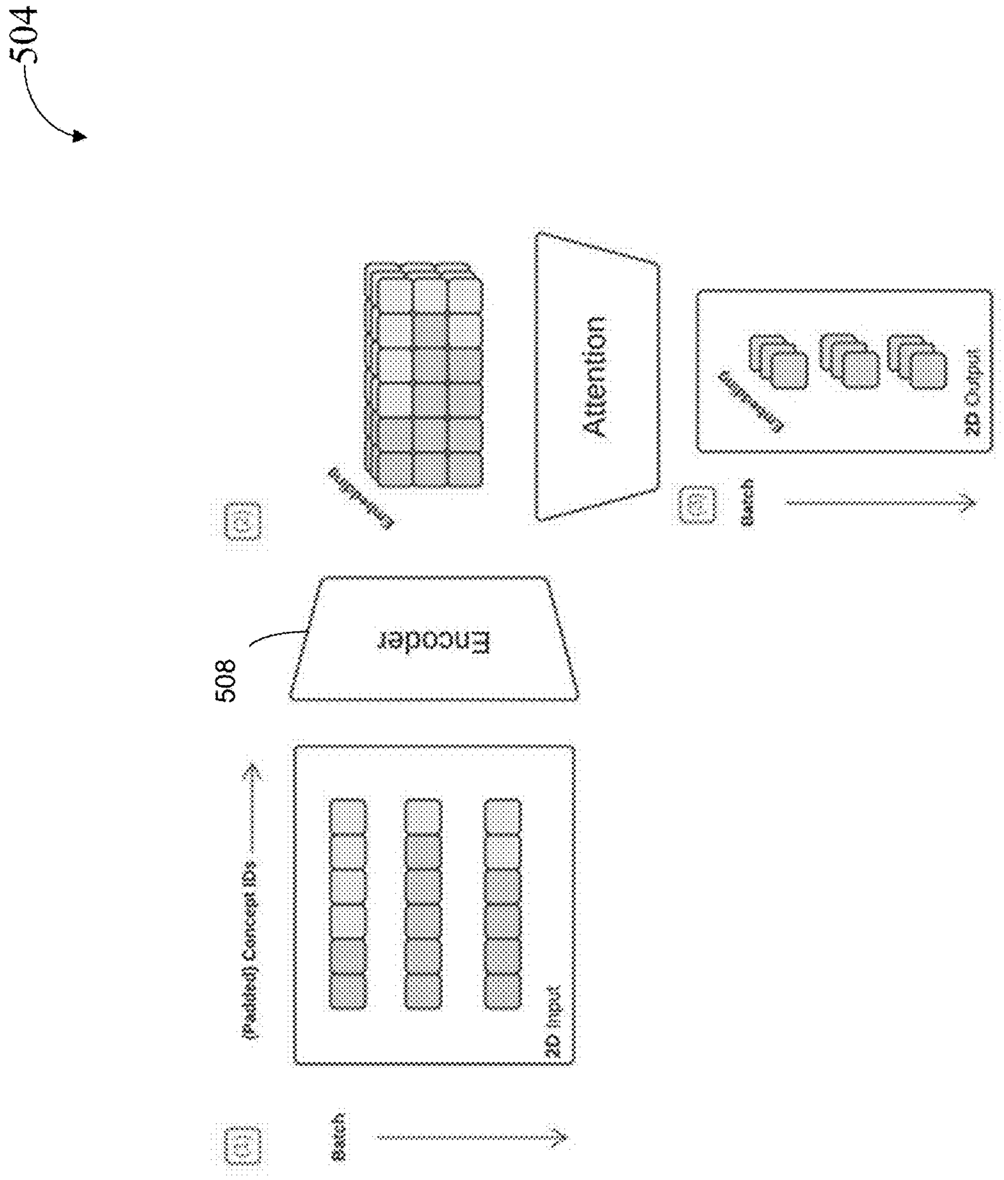
FIG. 5C shows an example architecture with a concept encoder in accordance with some embodiments of the present disclosure.

FIG. 5B shows an example architecture 502 with a snippet encoder, according to some embodiments. FIG. 5C shows an example architecture 504 with a concept encoder, according to some embodiments. In some embodiments, the encoder 208 includes a snippet encoder and a concepts encoder. A snippet encoder obtains a collection of snippet tokens per episode and produces a single embedding per episode. A concepts encoder obtains a collection of concept tokens per episode and also produces a single embedding per episode.

Referring to FIG. 5B, as shown by label (1), the snippet encoder expects as an input a three-dimensional (3D) tensor of shape (batch_size, max_snippet_len, max_num_snippets). Each episode contains a collection of max_num_snippets, number of snippets, each of which contain max_snippet_len, number of tokens per snippet. The values themselves are token identifiers that are mapped to a vocabulary of token embeddings. Note that it is highly unlikely that for a given episode one finds the same number of snippets, let alone snippets of the exact same length (unless the exact same number of tokens for each snippet is extracted). Hence, it is fair to assume some amount of padding to conform to these dimensions. The pad token will be ignored during model training.

In step (2), the 3D tensor is flattened into a two-dimensional (2D) tensor of shape (batch_size*max_num_snippets, max_snippet_length) before feeding it through the snippet encoder. The snippet encoder's task is to convert each token in a sequence into a learned representation. While information within a snippet is useful in this encoding task, each snippet should be treated independently, and therefore the first dimension is collapsed into max_num_snippets sized blocks of snippets per episode. Another motivation for this transform is practical: the snippet encoder (usually a pre-trained transformer) expects a 2D tensor and will error out otherwise.

In step (3), the flattened tensor is fed into a snippet encoder 506, which may be a transformer-based encoder architecture, such as BERT. The output of this encoder is the last hidden state of the model, a 3D tensor of shape (batch_size*max_num_snippets, max_snippet_length, dim_model), where dim_model is the length of the dense representations produced by the encoder. This can be thought of as a collection of embeddings produced by the model.

In step (4), a goal is to distill this 3D (four-dimensional (4D) if the first dimension is unpacked) into a single embedding per episode (i.e., 2D tensor). The first pass of summarizing this object is through token-level attention. The attention mechanism is a learned summarization of a collection on inputs. The intra-snippet attention summarizes max_snippet_length—the collection of embeddings per snippet—into a single vector. After passing through this layer, the output is (batch_size*max_num_snippets, dim_model).

In step (5), after obtaining this 2D tensor of shape (batch_size*max_num_snippets, dim_model), some embodiments re-extract the max_num_snippets dimension. This layer re-pops out that dimension such that the output is (batch_size,max_num_snippets,dim_model). In this tensor, there are max_num_snippets number of embeddings per episode of length dim_model.

In step (6), the architecture leverages a same attention mechanism (as the one used for token attention) to conduct inter-snippet attention. The max_num_snippets dimension is collapsed into a single representation. After passing through this layer, the final output is (batch_size, dim_model), which is a single embedding per episode.

Referring next to FIG. 5C, as indicated by label (1), a concept encoder expects as an input a 2:1) tensor of shape (batch size, max_concepUengfh). Each episode contains a collection of max_num_snippets number of concepts. The values in this tensor are token identifiers that are mapped to a vocabulary of concept embeddings. Note that it is highly unlikely that each episode contains an identical number of concepts, so just as in the case of the snippets input, there is padding. A concept encoder 502 includes an embedding layer. In step (2), the 2D collection of concept identifiers are then passed into the embedding layer that acts as a look-up table of concept embeddings. The output of this is a 3D tensor of shape (batch_size, max_concept_length, dim_model). In step (3), for concepts-level attention, similar to the snippet attention, the goal is to learn a weighted sum of the concepts into a single representation per episode. This layer transforms the (batch_size, max_concept_length, dim_model) into a final output of shape (batch_size, dim_model).

Figure 6:
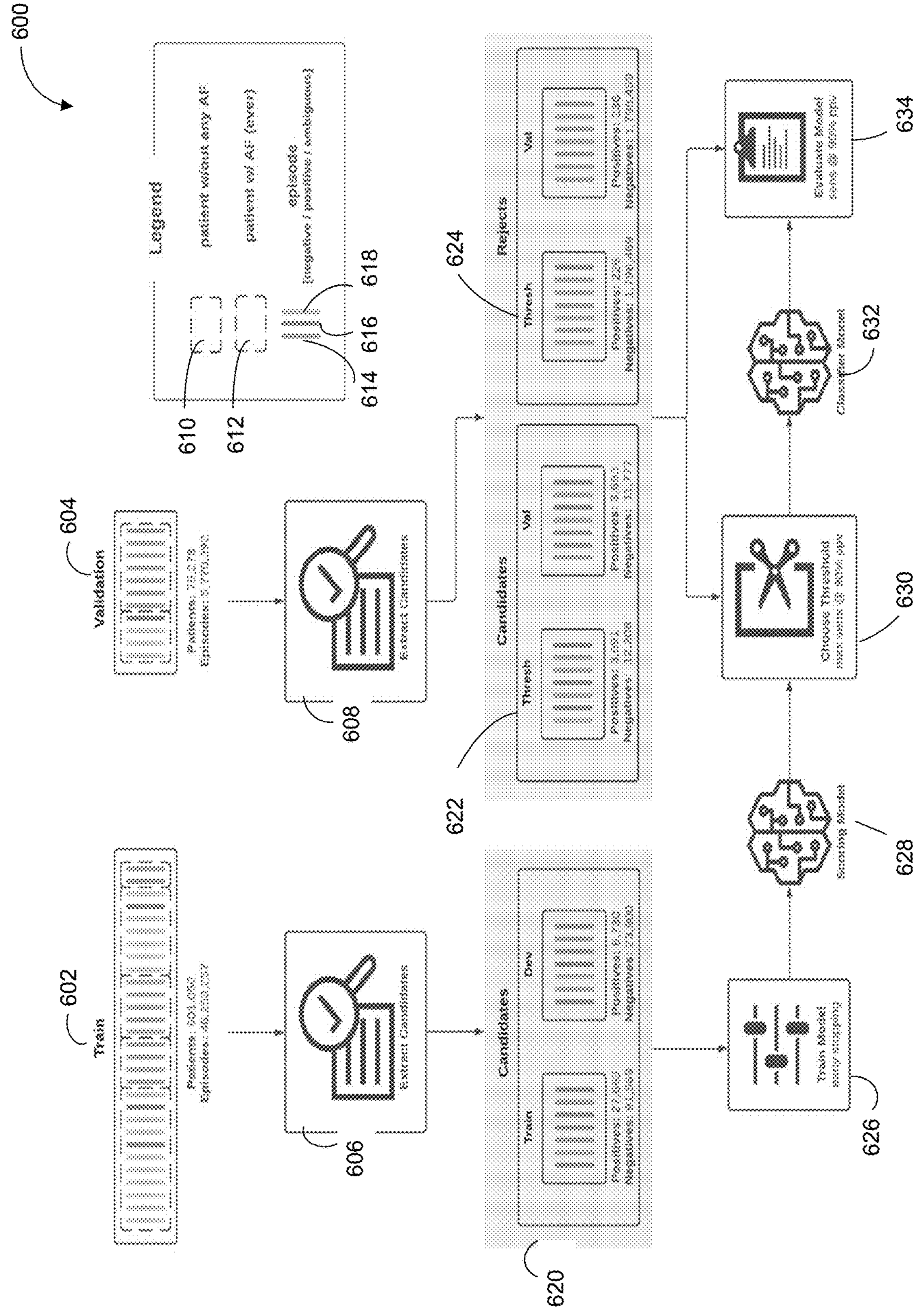
FIG. 6 shows a schematic diagram for an example training flow in accordance with some embodiments of the present disclosure.

FIG. 6 shows a schematic diagram for an example training flow 600, according to some embodiments. The training flow may be used to train the classifier 224 described above in reference to FIG. 2. The training flow may be performed using the training module 58. Alternatively, or additionally, another computer system may be used for the training in which case only the parameters for the classifier 50 may be retrieved and stored in the memory 92 and/or 90.

In some embodiments, a training dataset 602 and a validation dataset 604 each include episodes for patients. The datasets include episodes for patients without any clinical condition (in this example, AFib) shown within boxes 610, episodes for patients with the clinical condition shown within boxes 612. Each episode may correspond to a negative 614, positive 616, or an ambiguous 618 indication for the clinical condition. Extraction step 606 extracts (e.g., using the extractor 204) candidate episodes 620 from the training dataset 602. Extraction step 608 extracts (e.g., using the extractor 204) candidate episodes 622 and reject episodes 624 from the validation dataset 604. The extracted candidate episodes 620 are used to train (626) a model (e.g., the classifier 224). A scoring model 628 is used to score the model being trained. The candidates 622 and the rejects 624 are used to choose a threshold 630 (e.g., maximum sensitivity at 90% PPV), to obtain a trained model 632. The candidates 622 and the rejects 624 are also used to evaluate (634) (e.g., evaluated with sensitivity at 90% PPV) the trained model 632.

Figure 7:
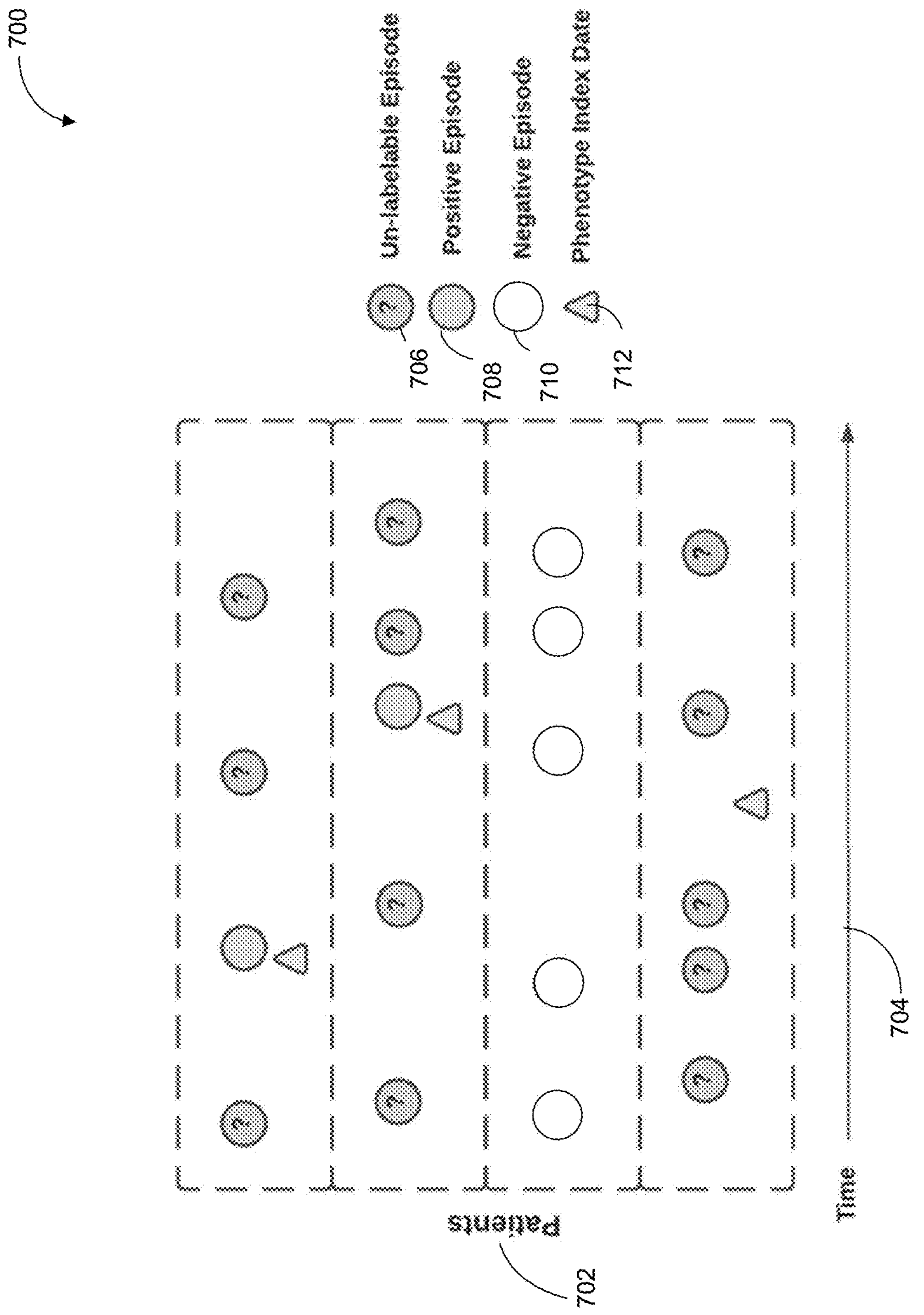
FIG. 7 shows example labels 700 for datasets used in training a classifier in accordance with some embodiments of the present disclosure.
Figure 8A:
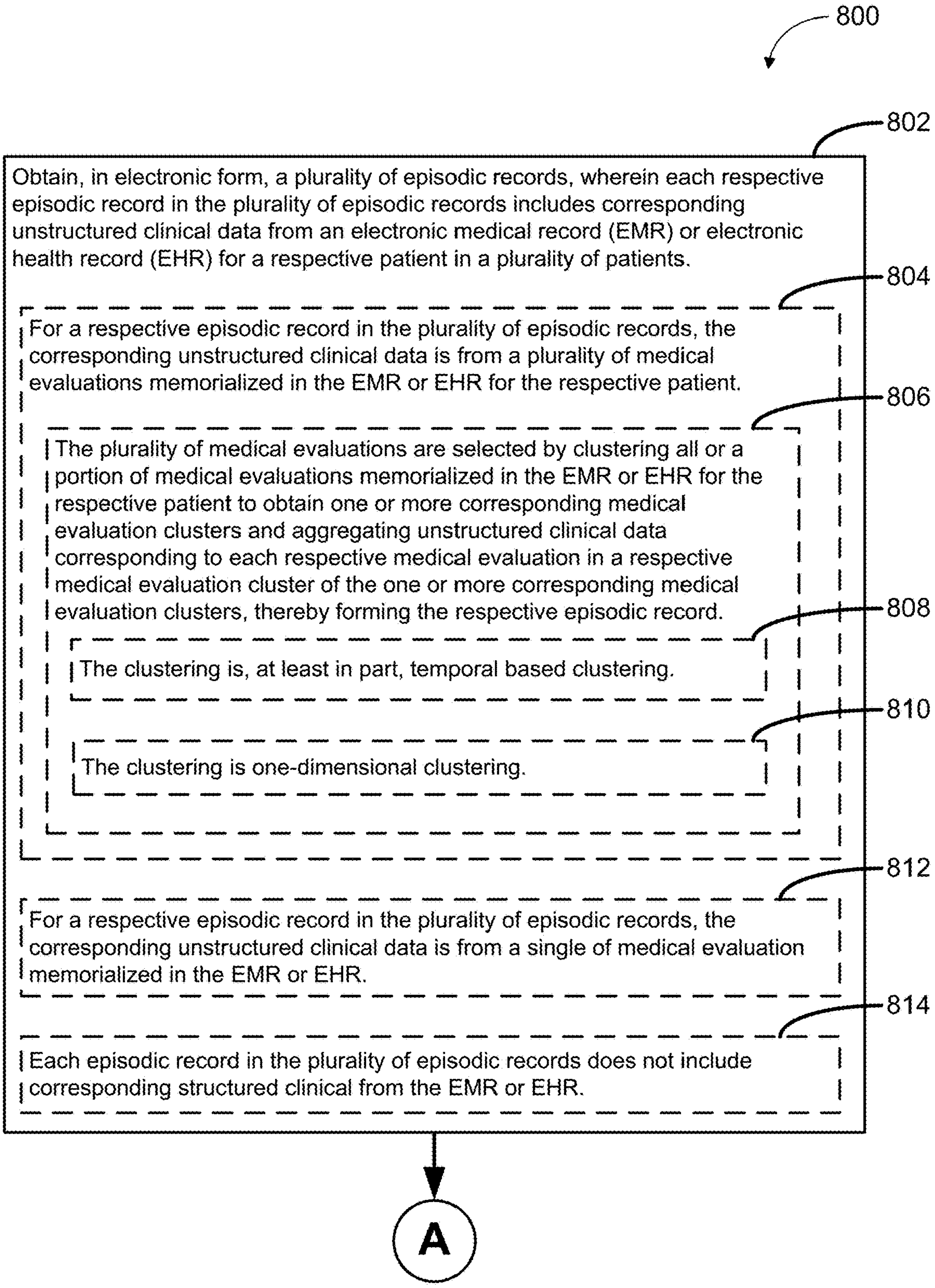
Figure 8B:
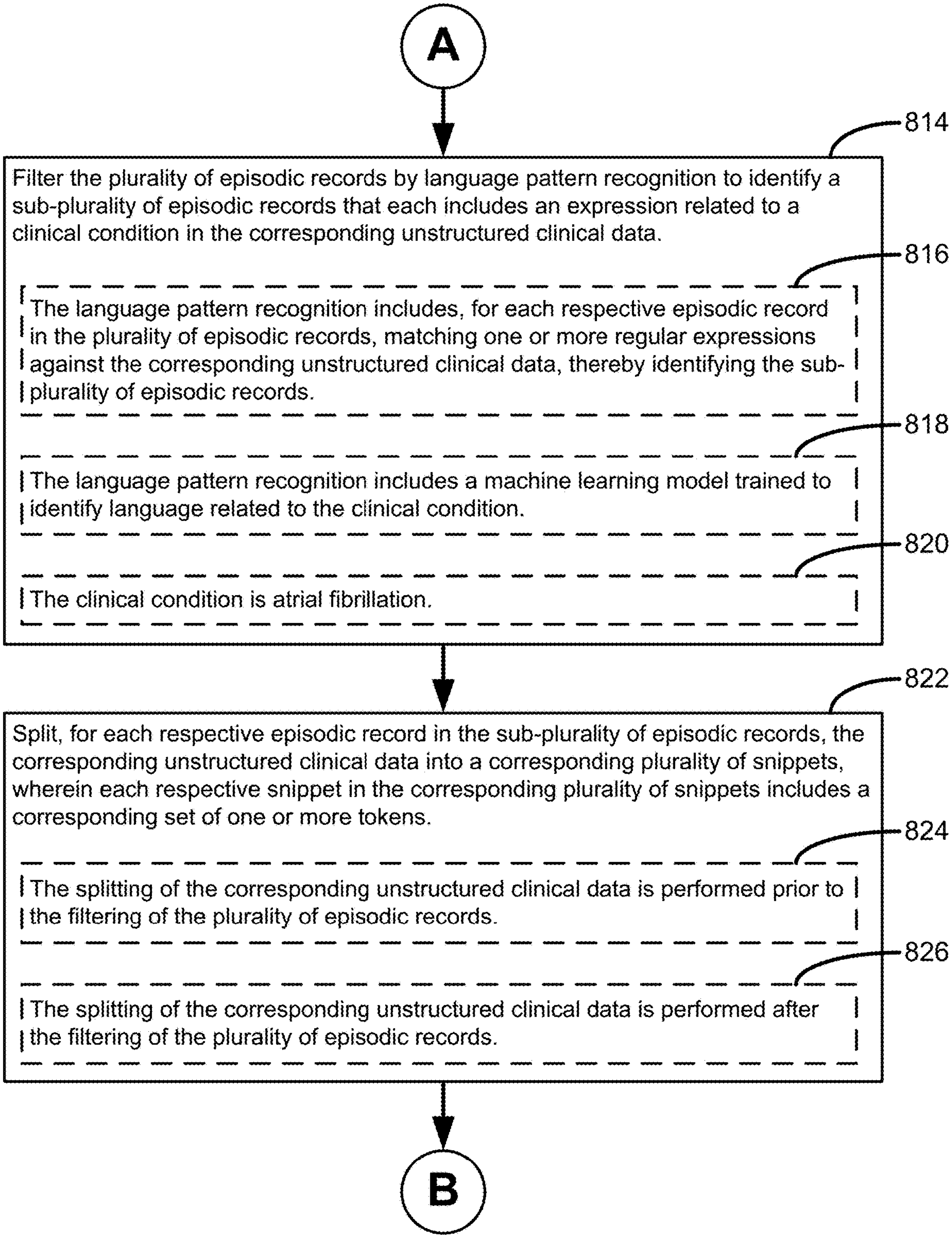
Figure 8C:
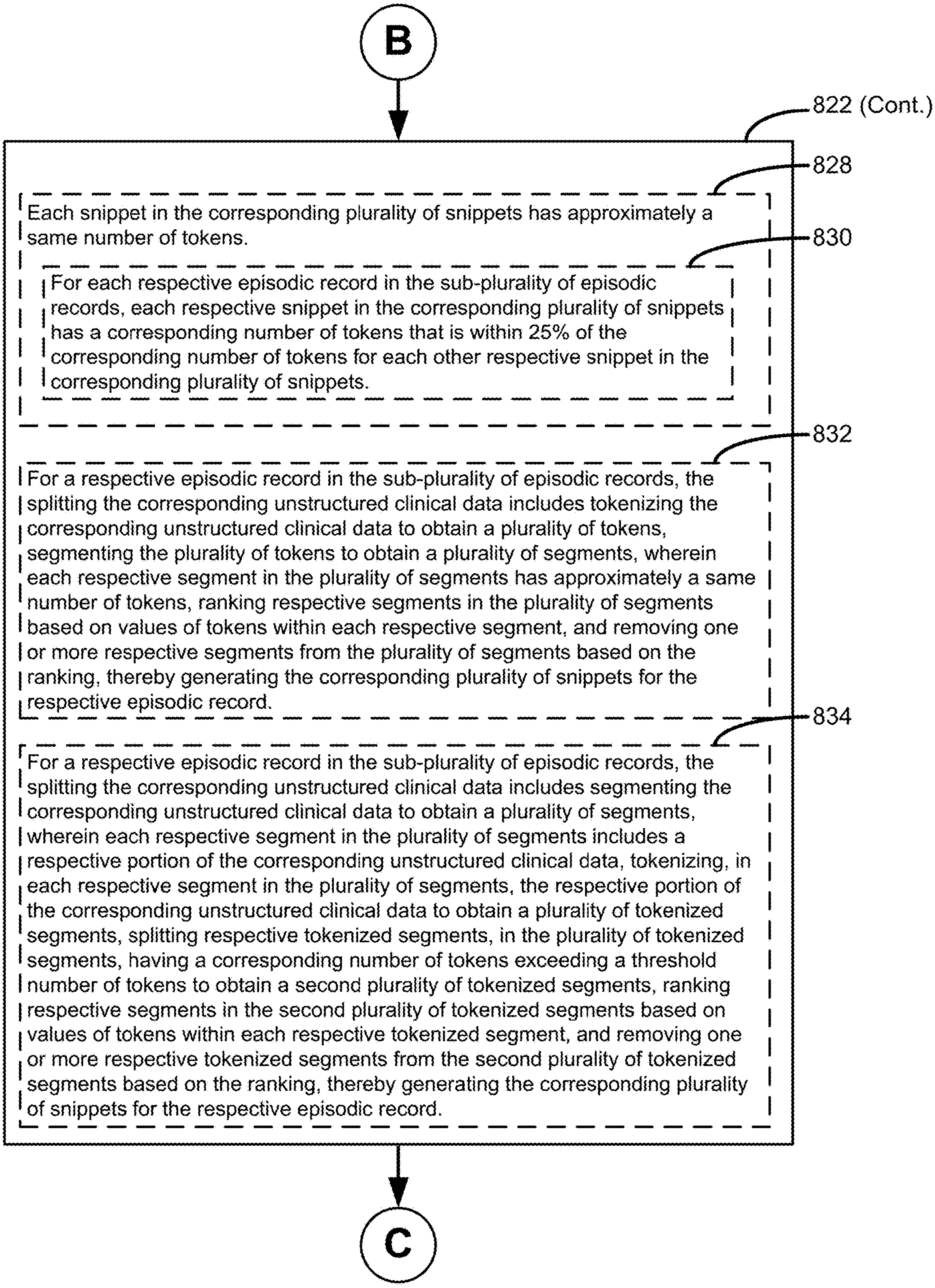
Figure 8D:
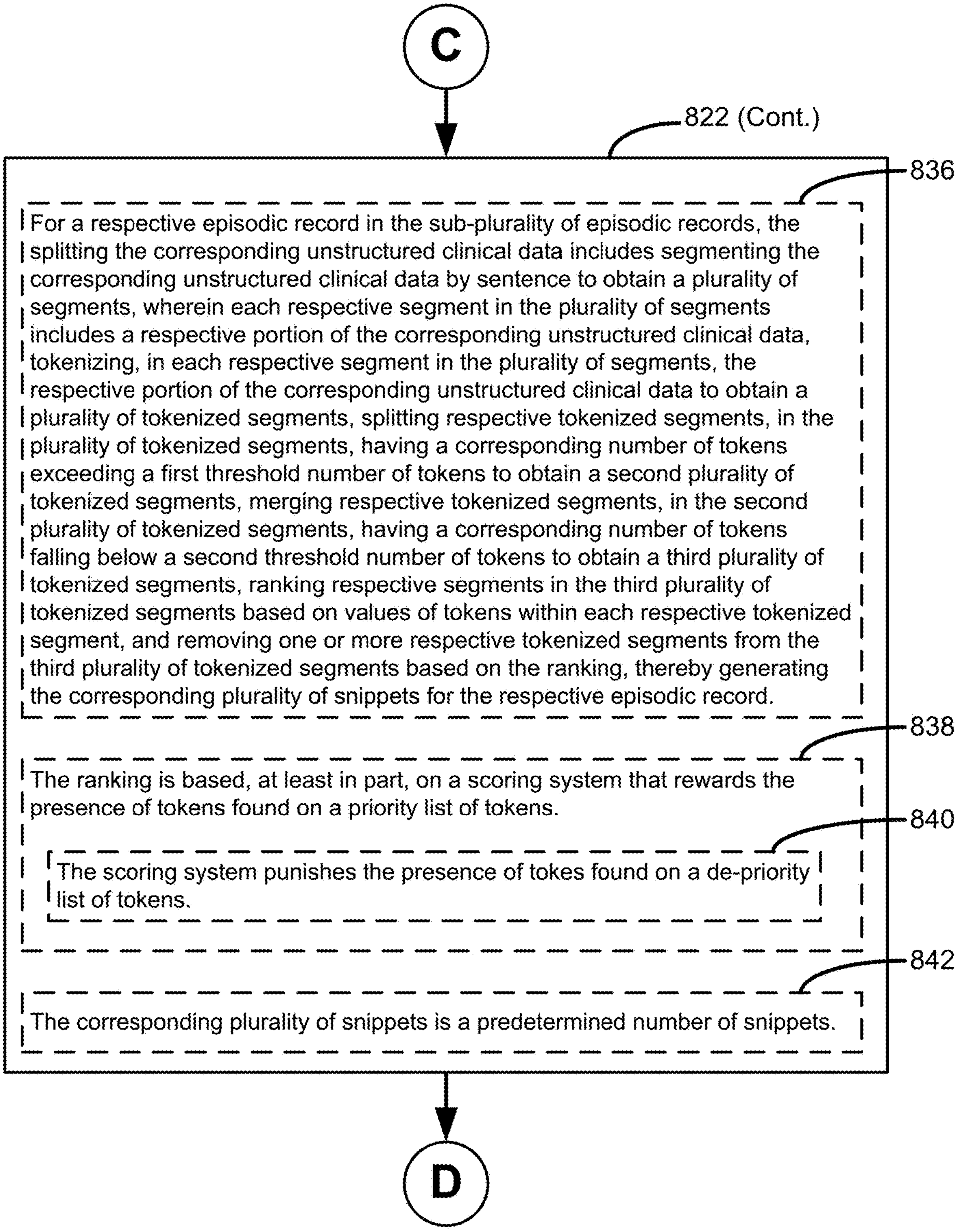
Figure 8F:
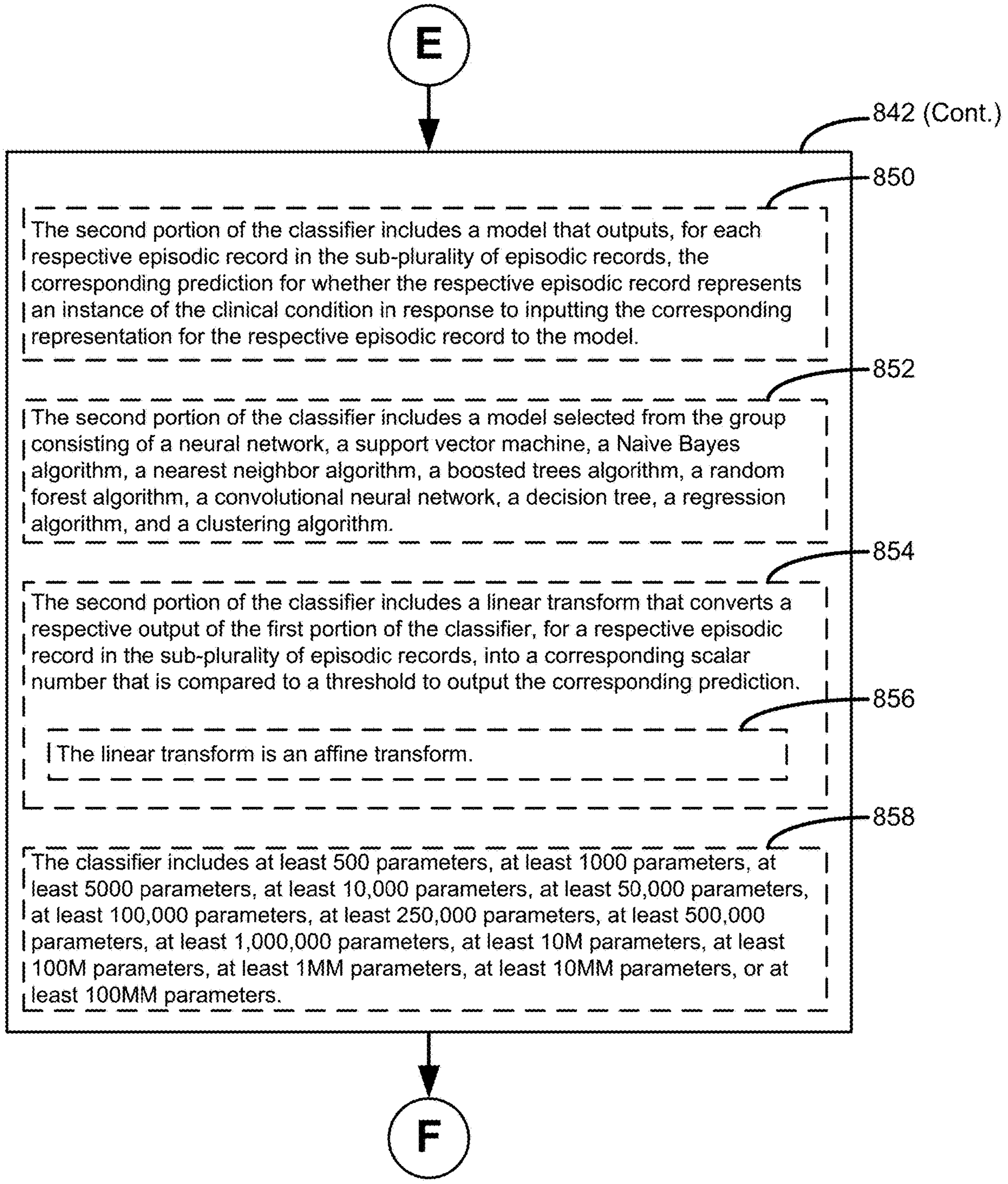
Figure 8G:
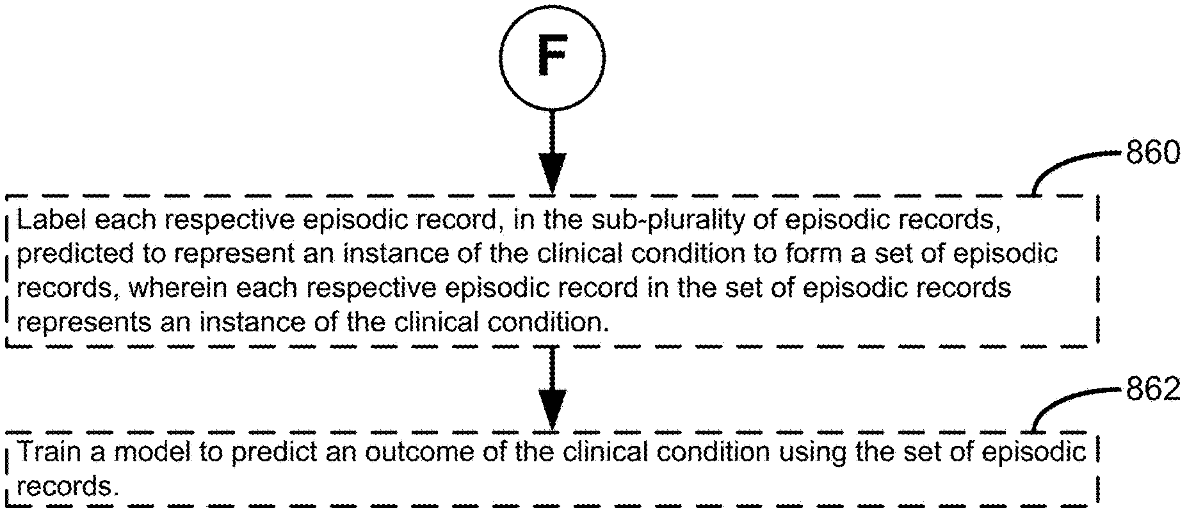

FIG. 7 shows example labels 700 for datasets used in training a classifier, according to one or more embodiments. Each patient 702 is associated with a corresponding set of episodes, each episode corresponds to a time interval (time is shown on axis 704). Each episode is labeled as (or identified as) a positive episode 708, a negative episode 710, or an un-labelable episode 706. Phenotype index dates 712, e.g., the first date a phenotype was identified for a patient (e.g., from the structured phenotype; in other words, the first occurrence of the clinical condition) may also be identified during the labeling process.

In some embodiments, "positive" labels are only assigned to those cases where an episode coincides with the first occurrence of a clinical condition in the EHR or EMR (e.g., as determined by the structured phenotype). This is because later occurrences (as determined by the structured phenotype) often are just picked up from some clinical history, but not recorded in the notes since the later episodes are usually for unrelated issues. Similarly, in some embodiments, "negative" labels are only assigned to EHR and EMR of patients who have never been identified as having the clinical condition (e.g., from the structured phenotype).

In some embodiments, the training module 58 performs the following steps for training the classifier 50. The training module 58 may cause the input output module 64, the language pattern recognition module 40, the splitting module 44, and/or the clustering module 56, to perform one or more of these steps, for training the classifier 50. The input output module 64 obtains, in electronic form, a plurality of episodic records (e.g., records in the training datasets 62). Each episodic record in the plurality of episodic records (i) comprises corresponding unstructured clinical data from an electronic medical record (EMR) or electronic health record (EHR) for a respective patient in a plurality of patients, and (ii) is associated with a corresponding date range. The training module 58 assigns, for each episodic record in the plurality of episodic records, a corresponding label 60 for whether the respective episodic record represents an instance of a clinical condition by at least determining whether corresponding structured data in the EMR or EHR includes a medical code that (i) is associated with the clinical condition, and (ii) is associated with the corresponding date range, thereby identifying (i) a first sub-plurality of episodic records with assigned labels that are positive for the clinical condition, and (ii) a second sub-plurality of episodic records with assigned labels that are negative for the clinical condition. The splitting module 44 splits, for each episodic record in the first sub-plurality of episodic records and the second sub-plurality of episodic records, the corresponding unstructured clinical data into a corresponding plurality of snippets, wherein each snippet in the corresponding plurality of snippets has approximately a same number of tokens. The training module 58 inputs, for each episodic record in the first sub-plurality of episodic records and the second sub-plurality of episodic records, the corresponding plurality of snippets for the respective episodic record to an untrained or partially trained model (e.g., the aggregation module 52) that applies, independently for each snippet in the plurality of corresponding snippets, a corresponding weight to the respective snippet via an attention mechanism. The untrained or partially trained model comprises a plurality of parameters that are learned during the training. The parameters are used to obtain a corresponding prediction for whether the respective episodic record represents an instance of the clinical condition as output from the model. The training module 58 uses, for each episodic record in the first sub-plurality of episodic records and the second sub-plurality of episodic records, a comparison between (i) the corresponding prediction output from the model, and (ii) the corresponding label, to update all or a subset of the plurality of parameters, thereby training the model to identify episodic records representing an instance of the clinical condition.

In some embodiments, the training module 58 further identifies a third plurality of episodic records with assigned labels that are indeterminable for the clinical condition. For example, some phenotypes (e.g., a complex stroke case) may not be identifiable from clinical records. For example, an attending physician may not have made the final diagnosis clear in the notes. In some embodiments, such records are labeled as indeterminable, rather than positive or negative.

In some embodiments, the training module 58 performs the following operations, for a respective episodic record in the plurality of episodic records: (a) when the corresponding EMR or EHR includes a medical code that (i) is associated with the clinical condition, and (ii) is associated with the corresponding date range, assigning a corresponding label that is positive for the clinical condition; (b) when the corresponding EMR or EHR does not include a medical code that (i) is associated with the clinical condition, and (ii) is associated with any date range, assigning a corresponding label that is negative for the clinical condition; and (c) when the corresponding EMR or EHR includes a medical code that (i) is associated with the clinical condition, and (ii) is associated with a respective date range that is after the corresponding date range, assigning a corresponding label that is indeterminable for the clinical condition.

In some embodiments, the training module 58 performs the following operations, for the respective episodic record: when the corresponding EMR or EHR includes a medical code that (i) is associated with the clinical condition, and (ii) is associated with a respective date range that precedes the corresponding date range, assigning a corresponding label that is indeterminable for the clinical condition.

The extractor-classifier network described herein may be used as a phenotype model for identifying patients with diseases, and/or for identifying other inclusion or exclusion criteria in population health platforms. Further, the extractor-classifier network may be used in other commercial applications, such as data structuring and phenotype-as-a-service for generating disease cohorts, for identifying or defining other clinical entities of interest, such as medications, procedures, or devices. For a new hospital system, the techniques described herein may be used to identify a list of patients to exclude, and/or to identify a list of patients with a specific clinical condition to display in an initial patient funnel. The techniques may also be used to determine new diagnoses for a clinical condition by comparing output with earlier results. A patient funnel may be visualized, connecting model output to subsequent diagnoses. A patient funnel may be used to compare all episodes that are identified as disease diagnosis episodes to the output of a prior risk-prediction operation for a given episode. In this way, it is possible to check if the risk prediction is high for episodes that are eventually diagnosed with the disease.

In some embodiments, the phenotype model may be used for on-site deployment of medical devices. The model may be applied as inclusion or exclusion criteria for patient cohort selection. Third parties including healthcare systems, providers, researchers, and pharmaceutical and medical technology companies require phenotypes in order to conduct clinical analysis. Those who have access to clinical notes may use the techniques described herein to generate more accurate phenotypes or to define their various patient cohorts or outcomes. These techniques may be used in any population health management tool, prediction algorithm, retrospective research, initial patient filtering or identification for prospective studies, such as clinical trials, or to improve services provided by electronic health records.

In some embodiments, the model described herein identifies whether a given chunk of text includes a positive attribution of a disease to a patient. Canonical positive examples include positive mentions of a clinical condition, such as "Patient was diagnosed with <clinical condition> on ECG," "Patient presents with clinical condition currently," "Patient was previously diagnosed with clinical condition," "Patient has history of clinical condition." Canonical negative examples include no mention of clinical condition, and incidental mentions of clinical condition (e.g., "Patient is at risk for developing clinical condition," "Patient has a family history of clinical condition"). Using atrial fibrillation (AFib) as an example, negative examples may include "Patient was suspected of having AFib, but presents in normal sinus rhythm," "No AFib or atrial flutter found."

FIGS. 8A-8G show a flowchart for an example method 800 for phenotyping clinical data, according to some embodiments. The method is performed by modules of the computer system 100 as detailed below.

Referring to block 802, in some embodiments, the input output module 64 obtains, in electronic form, a plurality of episodic records. Each respective episodic record in the plurality of episodic records includes corresponding unstructured clinical data from an electronic medical record (EMR) or electronic health record (EHR) for a respective patient in a plurality of patients. In general, an EMR or an EHR includes both structured data (e.g., billing codes) and unstructured data (e.g., clinical notes). The input output module 64 may select only the unstructured data from the EMR or EHR for a patient.

Referring to block 804, in some embodiments, for a respective episodic record in the plurality of episodic records, the input output module 64 obtains the corresponding unstructured clinical data from a plurality of medical evaluations memorialized in the EMR or EHR for the respective patient.

Referring to block 806, in some embodiments, the clustering module 56 selects the plurality of medical evaluations by clustering all or a portion of medical evaluations memorialized in the EMR or EHR for the respective patient to obtain one or more corresponding medical evaluation clusters and aggregating unstructured clinical data corresponding to each respective medical evaluation in a respective medical evaluation cluster of the one or more corresponding medical evaluation clusters, thereby forming the respective episodic record.

Referring to block 808, in some embodiments, the clustering is, at least in part, temporal based clustering (e.g., clustering based on the dates of medical evaluations memorialized in an EMR or EHR).

Referring to block 810, in some embodiments, the clustering is one-dimensional clustering. Various clustering methods may be used, such as kernel density estimation (KDE), sliding window, and machine learning.

Referring to block 812, in some embodiments, for a respective episodic record in the plurality of episodic records, the input output module 64 obtains the corresponding unstructured clinical data from a single of medical evaluation memorialized in the EMR or EHR.

Referring to block 814, in some embodiments, each episodic record in the plurality of episodic records does not include corresponding structured clinical from the EMR or EHR. Some embodiments do not include structured data. Some embodiments include such data depending on the application (e.g., the application requires analysis of specific structured data, such as billing codes). Notes-only models or models that use unstructured data generalize better than models that use only structured data.

Referring to block 814, in some embodiments, the language pattern recognition module 40 filters the plurality of episodic records by language pattern recognition to identify a sub-plurality of episodic records that each includes an expression related to a clinical condition in the corresponding unstructured clinical data.

Referring to block 816, in some embodiments, the language pattern recognition includes, for each respective episodic record in the plurality of episodic records, matching one or more regular expressions against the corresponding unstructured clinical data, thereby identifying the sub-plurality of episodic records. Examples of regular expressions are described above in reference to FIG. 2. More examples are available at developer.mozilla.org/en-US/docs/Web/JavaScript/Guide/Regular_Expressions/Cheatsheet, which is incorporated herein by reference.

Referring to block 818, in some embodiments, the language pattern recognition includes a machine learning model trained to identify language related to the clinical condition. In some embodiments, the trained machine learning model has high-recall and can reduce an input set of episodic records to a universe of candidates with higher prevalence than the input set.

Referring to block 820, in some embodiments, the clinical condition is atrial fibrillation. The techniques described herein may be used for phenotyping any clinical disease, condition, or clinical state (e.g., presence of a device-like ICD/pacemaker, occurrence of a procedure or test, any diagnosis, medications). The natural language processing techniques described herein may be used to phenotype heart failures, strokes, transient ischemic attack, myocardial infarction (heart attacks).

Referring to block 822, in some embodiments, the splitting module 44 splits, for each respective episodic record in the sub-plurality of episodic records, the corresponding unstructured clinical data into a corresponding plurality of snippets. Each respective snippet in the corresponding plurality of snippets includes a corresponding set of one or more tokens.

Referring to block 824, in some embodiments, the splitting of the corresponding unstructured clinical data is performed prior to the filtering of the plurality of episodic records.

Referring to block 826, in some embodiments, the splitting module 44 splits the splitting of the corresponding unstructured clinical data after the filtering of the plurality of episodic records.

Referring to block 828, in some embodiments, each snippet in the corresponding plurality of snippets has approximately a same number of tokens.

Referring to block 830, in some embodiments, for each respective episodic record in the sub-plurality of episodic records, each respective snippet in the corresponding plurality of snippets has a corresponding number of tokens that is within 25% of the corresponding number of tokens for each other respective snippet in the corresponding plurality of snippets. In some embodiments, the snippets are of different sizes, but may be padded to a set size (e.g., 512 snippets times 256 tokens per snippet). The size may be determined based on computation constraints (e.g., larger the amount of compute resources, larger the snippet size and/or number of snippets). In some embodiments, since each token is aggregated using intra-attention, there is no requirement of any distribution on tokens.

Referring to block 832, in some embodiments, for a respective episodic record in the sub-plurality of episodic records, the splitting module 44 splits the corresponding unstructured clinical data by: (i) tokenizing the corresponding unstructured clinical data to obtain a plurality of tokens; (ii) segmenting the plurality of tokens to obtain a plurality of segments. Each respective segment in the plurality of segments has approximately a same number of tokens; (iii) ranking respective segments in the plurality of segments based on values of tokens within each respective segment; and (iv) removing one or more respective segments from the plurality of segments based on the ranking, thereby generating the corresponding plurality of snippets for the respective episodic record.

Referring to block 834, in some embodiments, for a respective episodic record in the sub-plurality of episodic records, the splitting module 44 splits the corresponding unstructured clinical data by: (i) segmenting the corresponding unstructured clinical data to obtain a plurality of segments. Each respective segment in the plurality of segments includes a respective portion of the corresponding unstructured clinical data; (ii) tokenizing, in each respective segment in the plurality of segments, the respective portion of the corresponding unstructured clinical data to obtain a plurality of tokenized segments; (iii) splitting respective tokenized segments, in the plurality of tokenized segments, having a corresponding number of tokens exceeding a threshold number of tokens to obtain a second plurality of tokenized segments; (iv) ranking respective segments in the second plurality of tokenized segments based on values of tokens within each respective tokenized segment; and (v) removing one or more respective tokenized segments from the second plurality of tokenized segments based on the ranking, thereby generating the corresponding plurality of snippets for the respective episodic record.

Referring to block 836, in some embodiments, for a respective episodic record in the sub-plurality of episodic records, the splitting module 44 splits the corresponding unstructured clinical data by: (i) segmenting the corresponding unstructured clinical data by sentence to obtain a plurality of segments. Each respective segment in the plurality of segments includes a respective portion of the corresponding unstructured clinical data; (ii) tokenizing, in each respective segment in the plurality of segments, the respective portion of the corresponding unstructured clinical data to obtain a plurality of tokenized segments; (iii) splitting respective tokenized segments, in the plurality of tokenized segments, having a corresponding number of tokens exceeding a first threshold number of tokens to obtain a second plurality of tokenized segments; (iv) merging respective tokenized segments, in the second plurality of tokenized segments, having a corresponding number of tokens falling below a second threshold number of tokens to obtain a third plurality of tokenized segments; (v) ranking respective segments in the third plurality of tokenized segments based on values of tokens within each respective tokenized segment; and (vi) removing one or more respective tokenized segments from the third plurality of tokenized segments based on the ranking, thereby generating the corresponding plurality of snippets for the respective episodic record.

Referring to block 838, in some embodiments, the ranking is based, at least in part, on a scoring system that rewards the presence of tokens found on a priority list of tokens. Terms that may be on a priority list include terms such as those found in Unified Medical Language System (UMLS)

Metathesaurus. Examples include cardiac, discharge summary, cardiology, apixaban, metoprolol, aspirin, physical exam, atrial, and heart failure.

Referring to block 840, in some embodiments, the scoring system punishes the presence of tokes found on a de-priority list of tokens. Some embodiments move snippets that contain prioritized snippets to the top of the priority list (without using a separate de-priority list). For example, if the number of snippets exceed a pre-specified maximum number of snippets (which is a rare occurrence), some embodiments truncate the bottom. Some embodiments de-prioritize terms related to patient advice sections (e.g., "don't smoke") or site-specific boilerplate language in the notes. Some embodiments data mine the notes and obtain user input regarding a top M snippets that recur across many different patients. It is possible such snippets are boilerplate and not so useful information. In some situations, there are automated or templated notes for patients who miss their appointments or get a reminder phone call. There are more administrative-type notes or case management notes that may be deprioritized. Some embodiments de-prioritize based on note type.

Referring to block 842, in some embodiments, the corresponding plurality of snippets is a predetermined number of snippets.

Example operations of the splitting module 44 are further described above in reference to FIGS. 4A, 4B, and 4C, according to some embodiments.

Referring to block 842, in some embodiments, the classifier 50 predicts, for each episodic record in the sub-plurality of episodic records, if the respective episodic record represents an instance of the clinical condition, based on the corresponding plurality of snippets for the respective episodic record. The classifier 50 includes a first portion (the aggregation module 52) and a second portion (the interpretation module 54). The first portion includes an aggregation function that aggregates the corresponding plurality of snippets to output a corresponding representation for the respective episodic record. The second portion interprets the corresponding representation to output a corresponding prediction for whether the respective episodic record represents an instance of the clinical condition.

Referring to block 844, in some embodiments, the first portion of the classifier 50 includes a multi-head encoder that outputs, for each respective snippet in the plurality of corresponding snippets for each respective episodic record in the sub-plurality of episodic records, a corresponding contextualized token tensor for each respective token in the corresponding set of one or more tokens, thereby forming a corresponding plurality of corresponding contextualized token tensors for the respective snippet.

Referring to block 846, in some embodiments, the first portion of the classifier 50 further includes a multi-headed intra-attention mechanism that aggregates, for each respective episodic record in the sub-plurality of episodic records, the corresponding plurality of corresponding contextualized token tensors for each respective snippet in the plurality of corresponding snippets to output a corresponding contextualized snippet tensor, thereby forming a corresponding plurality of corresponding contextualized snippet tensors for the respective episodic record.

Referring to block 848, in some embodiments, the first portion of the classifier 50 further includes an inter-attention mechanism that aggregates, for each respective episodic record in the sub-plurality of episodic records, the corresponding plurality of corresponding contextualized snippet tensors to output a corresponding contextualized episodic record tensor for the respective episodic record Referring to block 850, in some embodiments, the second portion of the classifier 50 includes a model that outputs, for each respective episodic record in the sub-plurality of episodic records, the corresponding prediction for whether the respective episodic record represents an instance of the clinical condition in response to inputting the corresponding representation for the respective episodic record to the model.

Referring to block 852, in some embodiments, the second portion of the classifier 50 includes a model selected from the group consisting of a neural network, a support vector machine, a Naive Bayes algorithm, a nearest neighbor algorithm, a boosted trees algorithm, a random forest algorithm, a convolutional neural network, a decision tree, a regression algorithm, and a clustering algorithm.

Referring to block 854, in some embodiments, the second portion of the classifier 50 includes a linear transform that converts a respective output of the first portion of the classifier, for a respective episodic record in the sub-plurality of episodic records, into a corresponding scalar number that is compared to a threshold to output the corresponding prediction.

Referring to block 856, in some embodiments, the linear transform is an affine transform.

Referring to block 858, in some embodiments, the classifier 50 includes at least 500 parameters, at least 1000 parameters, at least 5000 parameters, at least 10,000 parameters, at least 50,000 parameters, at least 100,000 parameters, at least 250,000 parameters, at least 500,000 parameters, at least 1,000,000 parameters, at least 10 M parameters, at least 100 M parameters, at least 1 MM parameters, at least 10 MM parameters, or at least 100 MM parameters.

Example operations of the classifier 50 are further described above in reference to FIGS. 5A, 5B, and 5C, according to some embodiments.

Referring to block 860, in some embodiments, the input output module 64 labels each respective episodic record, in the sub-plurality of episodic records, predicted to represent an instance of the clinical condition to form a set of episodic records, wherein each respective episodic record in the set of episodic records represents an instance of the clinical condition.

Referring to block 862, in some embodiments, the input output module 64 trains a model to predict an outcome of the clinical condition using the set of episodic records.

EXAMPLES

Unstructured clinical notes from EHR records labeled relative to atrial fibrillation, e.g., as positive (reflecting atrial fibrillation episodes) or negative (reflecting an episode that was not atrial fibrillation), were collected from a regional health system and split into a training set of roughly 29 million code-labeled episodes and a hold-out set of roughly 1.8 million code-labeled episodes. The training set was used to train a classifier comprising a pre-trained encoder (BERT, as described in Devlin J. et al., arXiv:1810.04805), a multi-headed intra-snippet attention mechanism, an aggregating inter-snippet attention mechanism, and a linear transform, e.g., as diagramed in FIG. 2.

Figure 9:
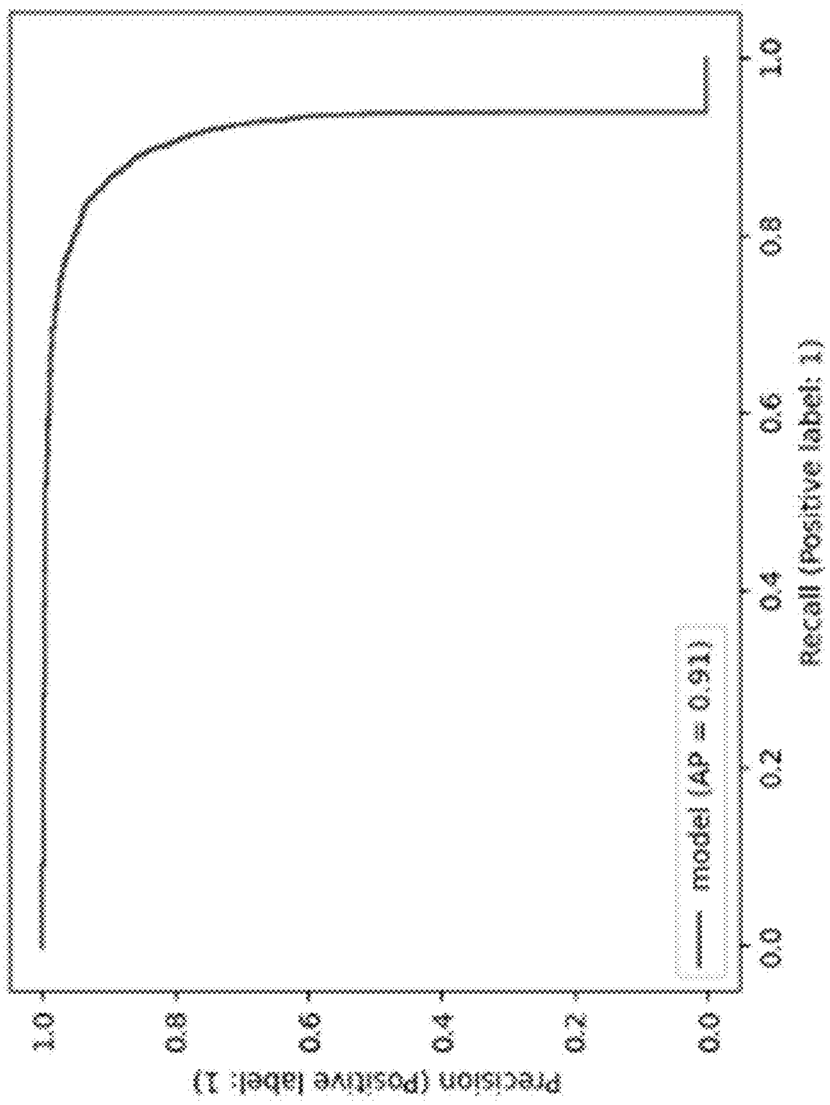
FIG. 9 shows validation set area under the precision-recall curve (AUPRC) for hold-out episodes in accordance with some embodiments of the present disclosure.

Model performance was computed using the code-based labels on the hold-out set, with un-extracted episodes scored as zero. Targeted blinded chart reviews of disagreements between the NLP model output and the code-based labels were also conducted. FIG. 9 shows validation set area under the precision-recall curve (AUPRC) for 1.8 million hold-out episodes, according to some embodiments. The NLP model achieved an AUPRC of 0.91. After thresholding, the NLP model achieved 87% recall and 89% precision. Blinded review of selected episodes showed that the NLP model was correct in 90% of disagreements where the code-based approach incorrectly labeled negative.

Figure 10:
FIG. 10 shows interpretable model results on hypothetical text snippets in accordance with some embodiments of the present disclosure.

FIG. 10 shows interpretable model results on hypothetical text snippets, according to some embodiments. The results demonstrate ability to distinguish between true positive and incidental atrial fibrillation mentions. Snippets outlined in green were labeled positive whereas snippets outlined in red were labeled negative. The heatmap behind each word represents model attention weights, with higher weight correlating with words the model found more important during classification.

In this way, NLP models can be used to learn to automatically label the presence or absence of clinical conditions, such as atrial fibrillation, within clinical notes. The systems and methods described herein can provide greater accuracy and generalizability relative to code-based labeling methods.

CONCLUSION

The foregoing description, for purposes of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A method for phenotyping clinical data, the method comprising:

obtaining, in electronic form, a plurality of episodic records, wherein each episodic record in the plurality of episodic records comprises corresponding unstructured clinical data from an electronic medical record (EMR) or electronic health record (EHR) for a respective patient in a plurality of patients;

filtering the plurality of episodic records by language pattern recognition to identify a sub-plurality of episodic records that each includes an expression related to a clinical condition in the corresponding unstructured clinical data;

splitting, for each episodic record in the sub-plurality of episodic records, the corresponding unstructured clinical data into a corresponding plurality of snippets, wherein each snippet in the corresponding plurality of snippets comprises a corresponding set of one or more tokens; and predicting, for each episodic record in the sub-plurality of episodic records, if the respective episodic record represents an instance of the clinical condition by inputting the corresponding plurality of snippets for the respective episodic record to a classifier comprising a first portion and a second portion, wherein the first portion comprises (i) a multi-head encoder that outputs, for each snippet in the corresponding plurality of snippets, a corresponding contextualized token tensor for each token in the corresponding set of one or more tokens, thereby forming a corresponding plurality of corresponding contextualized token tensors for the respective snippet, and (ii) an aggregation function that aggregates the corresponding plurality of snippets to output a corresponding representation for the respective episodic record, and wherein the second portion interprets the corresponding representation to output a corresponding prediction for whether the respective episodic record represents an instance of the clinical condition.

2. The method of claim 1, wherein, for a respective episodic record in the plurality of episodic records, the corresponding unstructured clinical data is obtained from a plurality of medical evaluations memorialized in the EMR or EHR for the respective patient.

3. The method of claim 2, wherein the plurality of medical evaluations are selected by (i) clustering all or a portion of medical evaluations memorialized in the EMR or EHR for the respective patient to obtain one or more corresponding medical evaluation clusters, and (ii) aggregating unstructured clinical data corresponding to each medical evaluation in a respective medical evaluation cluster of the one or more corresponding medical evaluation clusters, thereby forming the respective episodic record.

4. The method of claim 3, wherein the clustering is, at least in part, temporal based clustering.

5. The method of claim 3, wherein the clustering is one-dimensional clustering.

6. The method of claim 1, wherein, for a respective episodic record in the plurality of episodic records, the corresponding unstructured clinical data is obtained from a single of medical evaluation memorialized in the EMR or EHR.

7. The method of claim 1, wherein each episodic record in the plurality of episodic records does not include corresponding structured clinical data from the EMR or EHR.

8. The method of claim 1, wherein the language pattern recognition comprises, for each episodic record in the plurality of episodic records, matching one or more regular expressions against the corresponding unstructured clinical data, thereby identifying the sub-plurality of episodic records.

9. The method of claim 1, wherein the splitting of the corresponding unstructured clinical data is performed prior to the filtering of the plurality of episodic records.

10. The method of claim 1, wherein the splitting of the corresponding unstructured clinical data is performed after the filtering of the plurality of episodic records.

11. The method of claim 1, wherein each snippet in the corresponding plurality of snippets has approximately a same number of tokens.

12. The method of claim 1, wherein, for a respective episodic record in the sub-plurality of episodic records, the splitting the corresponding unstructured clinical data comprises:

tokenizing the corresponding unstructured clinical data to obtain a plurality of tokens, segmenting the plurality of tokens to obtain a plurality of segments, wherein each segment in the plurality of segments has approximately a same number of tokens;

ranking respective segments in the plurality of segments based on values of tokens within each segment, and removing one or more respective segments from the plurality of segments based on the ranking, thereby generating the corresponding plurality of snippets for the respective episodic record.

13. The method of claim 1, wherein, for each a respective episodic record in the sub-plurality of episodic records, the splitting the corresponding unstructured clinical data comprises:

segmenting the corresponding unstructured clinical data to obtain a plurality of segments, wherein each segment in the plurality of segments comprises a respective portion of the corresponding unstructured clinical data, tokenizing, in each segment in the plurality of segments, the respective portion of the corresponding unstructured clinical data to obtain a plurality of tokenized segments, splitting respective tokenized segments, in the plurality of tokenized segments, having a corresponding number of tokens exceeding a threshold number of tokens to obtain a second plurality of tokenized segments;

ranking respective segments in the second plurality of tokenized segments based on values of tokens within each tokenized segment, and removing one or more respective tokenized segments from the second plurality of tokenized segments based on the ranking, thereby generating the corresponding plurality of snippets for the respective episodic record.

14. The method of claim 1, wherein, for each a respective episodic record in the sub-plurality of episodic records, the splitting the corresponding unstructured clinical data comprises:

segmenting the corresponding unstructured clinical data by sentence to obtain a plurality of segments, wherein each segment in the plurality of segments comprises a respective portion of the corresponding unstructured clinical data, tokenizing, in each segment in the plurality of segments, the respective portion of the corresponding unstructured clinical data to obtain a plurality of tokenized segments, splitting respective tokenized segments, in the plurality of tokenized segments, having a corresponding number of tokens exceeding a first threshold number of tokens to obtain a second plurality of tokenized segments;

merging respective tokenized segments, in the second plurality of tokenized segments, having a corresponding number of tokens falling below a second threshold number of tokens to obtain a third plurality of tokenized segments;

ranking respective segments in the third plurality of tokenized segments based on values of tokens within each tokenized segment, and removing one or more respective tokenized segments from the third plurality of tokenized segments based on the ranking, thereby generating the corresponding plurality of snippets for the respective episodic record.

15. The method of claim 1, wherein the first portion of the classifier further comprises a multi-headed intra-attention mechanism that aggregates, for each episodic record in the sub-plurality of episodic records, the corresponding plurality of corresponding contextualized token tensors for each snippet in the plurality of corresponding snippets to output a corresponding contextualized snippet tensor, thereby forming a corresponding plurality of corresponding contextualized snippet tensors for the respective episodic record.

16. The method of claim 15, wherein the first portion of the classifier further comprises an inter-attention mechanism that aggregates, for each episodic record in the sub-plurality of episodic records, the corresponding plurality of corresponding contextualized snippet tensors to output a corresponding contextualized episodic record tensor for the respective episodic record.

17. The method of claim 16, wherein the second portion of the classifier comprises a model that outputs, for each episodic record in the sub-plurality of episodic records, the corresponding prediction for whether the respective episodic record represents an instance of the clinical condition in response to inputting the contextualized episodic record tensor for the respective episodic record to the model.

18. The method of claim 1, wherein the second portion of the classifier comprises a linear transform that converts a respective output of the first portion of the classifier, for a respective episodic record in the sub-plurality of episodic records, into a corresponding scalar number that is compared to a threshold to output the corresponding prediction.

19. The method of claim 18, wherein the linear transform is an affine transform.

20. A computer system comprising:

one or more processors; and a non-transitory computer-readable medium including computer-executable instructions that, when executed by the one or more processors, cause the processors to perform a method for phenotyping clinical data, the method comprising:

obtaining, in electronic form, a plurality of episodic records, wherein each episodic record in the plurality of episodic records comprises corresponding unstructured clinical data from an electronic medical record (EMR) or electronic health record (EHR) for a respective patient in a plurality of patients;

filtering the plurality of episodic records by language pattern recognition to identify a sub-plurality of episodic records that each includes an expression related to a clinical condition in the corresponding unstructured clinical data;

splitting, for each episodic record in the sub-plurality of episodic records, the corresponding unstructured clinical data into a corresponding plurality of snippets, wherein each snippet in the corresponding plurality of snippets comprises a corresponding set of one or more tokens; and predicting, for each episodic record in the sub-plurality of episodic records, if the respective episodic record represents an instance of the clinical condition by inputting the corresponding plurality of snippets for the respective episodic record to a classifier comprising a first portion and a second portion, wherein the first portion comprises (i) a multi-head encoder that outputs, for each snippet in the corresponding plurality of snippets, a corresponding contextualized token tensor for each token in the corresponding set of one or more tokens, thereby forming a corresponding plurality of corresponding contextualized token tensors for the respective snippet, and (ii) an aggregation function that aggregates the corresponding plurality of snippets to output a corresponding representation for the respective episodic record, and wherein the second portion interprets the corresponding representation to output a corresponding prediction for whether the respective episodic record represents an instance of the clinical condition.

21. A non-transitory computer-readable storage medium having stored thereon program code instructions that, when executed by a processor, cause the processor to perform a method for phenotyping clinical data, the method comprising:

obtaining, in electronic form, a plurality of episodic records, wherein each episodic record in the plurality of episodic records comprises corresponding unstructured clinical data from an electronic medical record (EMR) or electronic health record (EHR) for a respective patient in a plurality of patients;

filtering the plurality of episodic records by language pattern recognition to identify a sub-plurality of episodic records that each includes an expression related to a clinical condition in the corresponding unstructured clinical data;

splitting, for each episodic record in the sub-plurality of episodic records, the corresponding unstructured clinical data into a corresponding plurality of snippets, wherein each snippet in the corresponding plurality of snippets comprises a corresponding set of one or more tokens; and predicting, for each episodic record in the sub-plurality of episodic records, if the respective episodic record represents an instance of the clinical condition by inputting the corresponding plurality of snippets for the respective episodic record to a classifier comprising a first portion and a second portion, wherein the first portion comprises (i) a multi-head encoder that outputs, for each snippet in the corresponding plurality of snippets, a corresponding contextualized token tensor for each token in the corresponding set of one or more tokens, thereby forming a corresponding plurality of corresponding contextualized token tensors for the respective snippet, and (ii) an aggregation function that aggregates the corresponding plurality of snippets to output a corresponding representation for the respective episodic record, and wherein the second portion interprets the corresponding representation to output a corresponding prediction for whether the respective episodic record represents an instance of the clinical condition.

* * * * *